US006669960B2

(12) United States Patent
Etter

(10) Patent No.: US 6,669,960 B2
(45) Date of Patent: Dec. 30, 2003

(54) PARTICULATE DRUG-CONTAINING PRODUCTS AND METHOD OF MANUFACTURE

(75) Inventor: Jeffrey B. Etter, Boulder, CO (US)

(73) Assignee: RxKinetix, Inc., Louisville, CO (US)

( * ) Notice: Subject to any disclaimer, the term of this patent is extended or adjusted under 35 U.S.C. 154(b) by 53 days.

(21) Appl. No.: 09/740,573

(22) Filed: Dec. 18, 2000

(65) Prior Publication Data

US 2001/0036480 A1 Nov. 1, 2001

Related U.S. Application Data

(63) Continuation-in-part of application No. 09/604,786, filed on Jun. 26, 2000, now abandoned, which is a continuation-in-part of application No. 09/469,733, filed on Dec. 21, 1999.

(51) Int. Cl.[7] .............................................. A61K 9/14
(52) U.S. Cl. ...................... 424/489; 424/499; 424/43; 424/45; 424/400; 514/2; 514/3
(58) Field of Search ................. 424/489, 499, 424/43, 45, 400; 514/2, 3

(56) References Cited

U.S. PATENT DOCUMENTS

| 4,895,719 A | 1/1990 | Radhakrishnan et al. ..... 424/45 |
| 5,460,173 A | 10/1995 | Mulhauser et al. .... 128/203.15 |
| 5,503,869 A | 4/1996 | Van Oort ................... 427/2.14 |
| 5,619,984 A | 4/1997 | Hodson et al. ......... 128/203.15 |
| 5,654,007 A | 8/1997 | Johnson et al. ............. 424/489 |
| 5,770,559 A | 6/1998 | Manning et al. ................ 514/2 |
| 5,794,613 A | 8/1998 | Piskorski ............... 128/203.12 |
| 5,795,594 A | 8/1998 | York et al. .................. 424/489 |
| 5,814,678 A | 9/1998 | Randolph .................... 522/18 |
| 5,851,453 A | 12/1998 | Hanna et al. .................. 264/5 |
| 5,874,064 A | 2/1999 | Edwards et al. .............. 424/46 |
| 5,875,776 A | 3/1999 | Vaghefi ................. 128/203.15 |
| 5,997,848 A | 12/1999 | Patton et al. .................. 424/46 |
| 6,063,910 A | 5/2000 | Debenedetti et al. ....... 530/418 |
| 6,372,260 B1 * | 4/2002 | Andersson et al. ......... 424/501 |

FOREIGN PATENT DOCUMENTS

| EP | 0 069 715 B1 | 11/1986 |
| EP | 0 542 314 A1 | 11/1992 |
| EP | 0 542 314 B1 | 7/1998 |
| WO | WO 95/01221 | 1/1995 |
| WO | WO 96/00610 | 1/1996 |
| WO | WO 96/32149 | 10/1996 |
| WO | WO 98/04308 | 2/1998 |
| WO | WO 98/29141 | 7/1998 |
| WO | WO 98/36825 | 8/1998 |
| WO | WO 99/16419 | 4/1999 |
| WO | WO 99/59710 | 11/1999 |

OTHER PUBLICATIONS

"Drug Formulation Technology For Compounds Administered by Inhalation," Alliance Pharmaceutical Corp; Web Page www.allp.com/PulmoSpheres/PS_WHITE.HTM; publication date unknown.

(List continued on next page.)

Primary Examiner—James M. Spear
Assistant Examiner—Liliana Di Nola-Baron
(74) Attorney, Agent, or Firm—Marsh Fischmann & Breyfogle LLP

(57) ABSTRACT

Provided is a compressed anti-solvent technique for manufacture of drug-containing powders for pulmonary delivery. The drug is processed in a cosolvent system including two or more mutually soluble organic solvents. Also provided are powders manufacturable by the manufacture method, including powders of substantially pure drug and powders including a biocompatible polymer for pulmonary sustained drug release applications. Also provided are packaged products including drug-containing powder in a container that is receivable by and operable with a dry powder inhaler to produce an aerosol including dispersed drug-containing particles when the inhaler is actuated.

56 Claims, 9 Drawing Sheets

OTHER PUBLICATIONS

Figure 1:
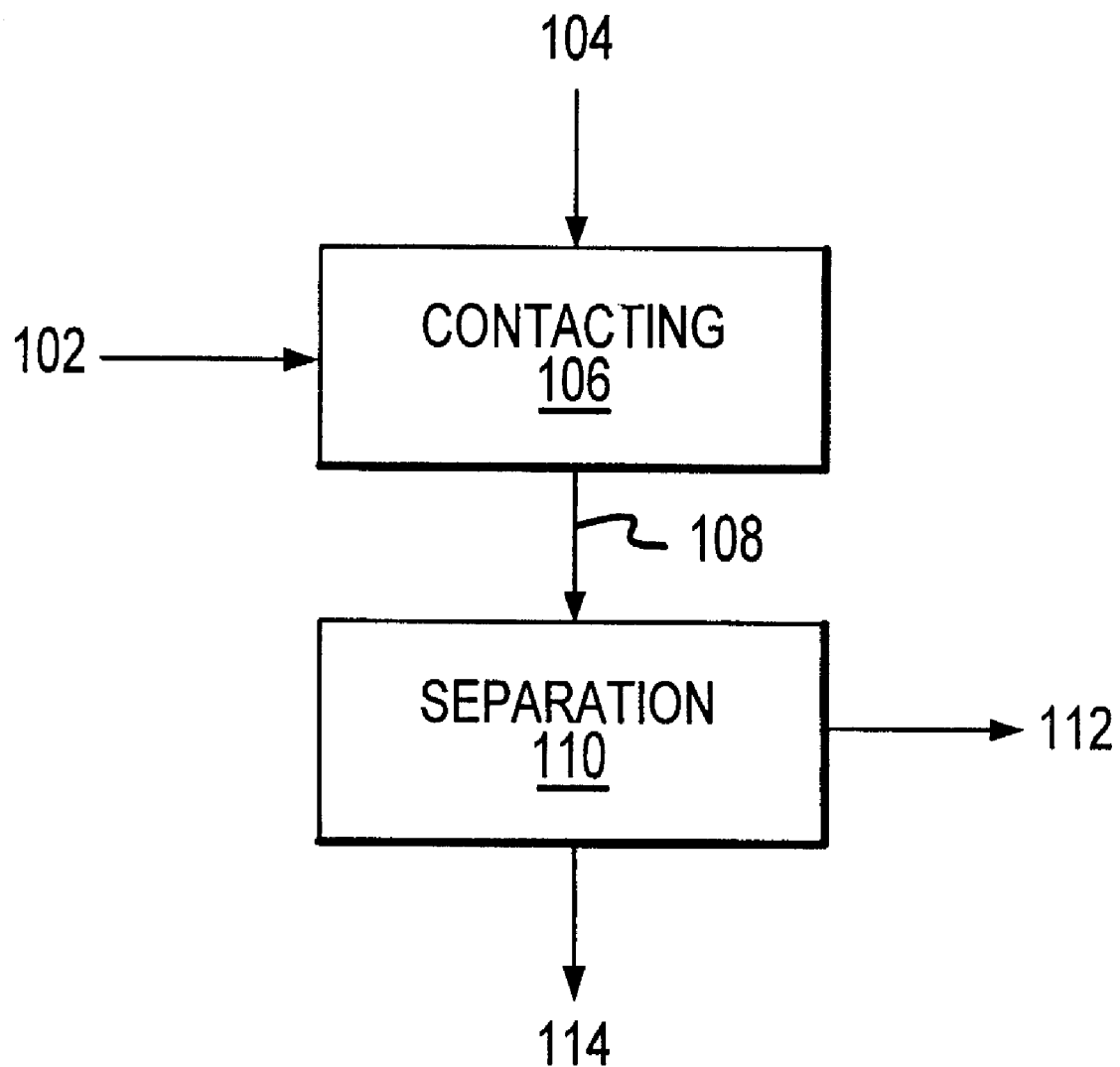

Zia, Hossein et al., "Comparison of Nasal Insulin Powders Prepared by Supercritical Fluid and Freeze–Drying Techniques," *Particulate Science and Technology*, 15:273–301 (1997).

Knutson, Barbara L. et al., "Preparation of Microparticulates Using Supercritical Fluids," *Drugs Pharm. Sci.*, 77:89–125 (1996).

Tom, Jean W. and Pablo G. Debenedetti, "Formation of Bioerodible Polymeric Microspheres and Microparticles by Rapid Expansion of Supercritical Solutions, " *Biotechnol. Prog.*, 1991, vol. 7, No. 5, pp. 403–411.

Winters, Michael A. et al., "Long–Term and High–Temperature Storage of Supercritically–Processed Microparticulate Protein Powders," *Pharm. Res.*, vol. 14, No. 10, 1997, pp. 1370–1378.

Winters, Michael A. et al., "Precipitation of Proteins in Supercritical Carbon Dioxide," *J. Pharmaceutical Sciences*, vol. 85, No. 6, Jun. 1996, pp. 586–594.

Yeo, Sang–Do et al., "Secondary Structure Characterization of Microparticulate Insulin Powders," *J. of Pharmaceutical Sciences*, vol. 83, No. 12, Dec. 1994, pp. 1651–1656.

Yeo, Sang–Do et al., "Formation of Microparticulate Protein Powders Using a Supercritical Fluid Antisolvent," *Biotechnology and Bioengineering*, vol. 41, No. 3, Feb. 5, 1993, pp. 341–346.

* cited by examiner

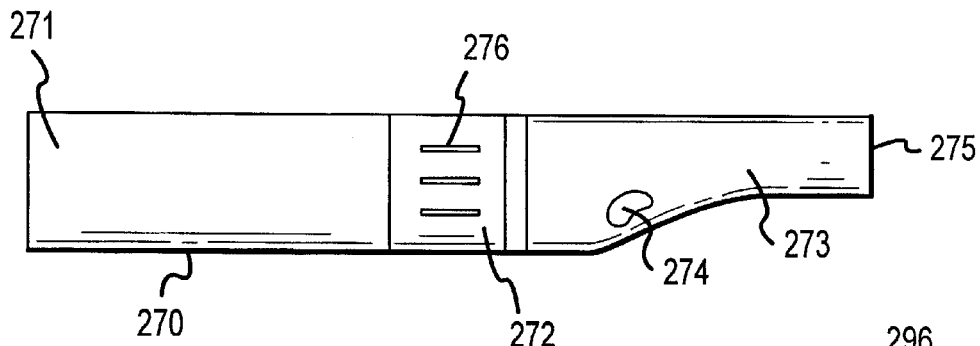
FIG.9
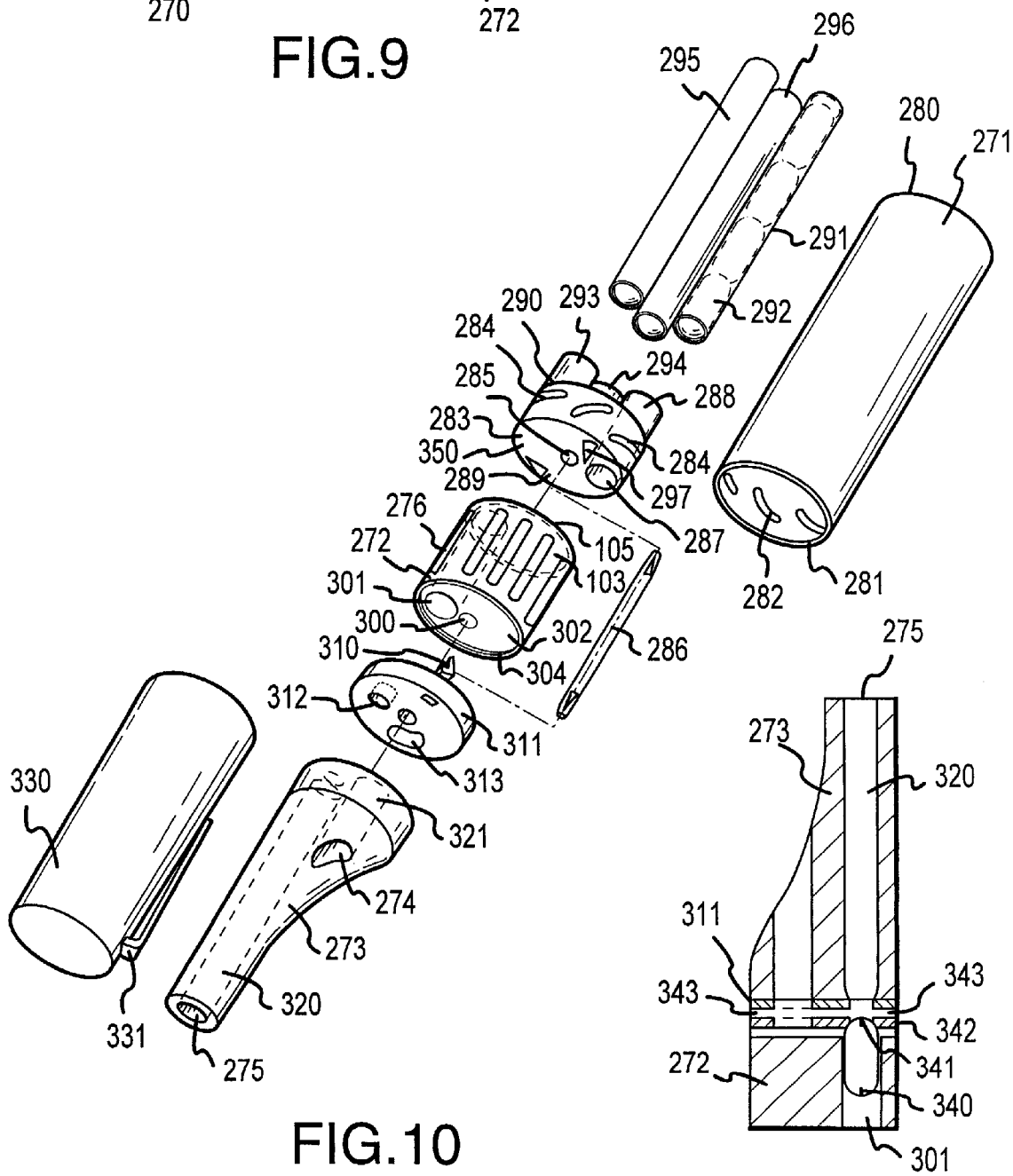
FIG.10
FIG.11

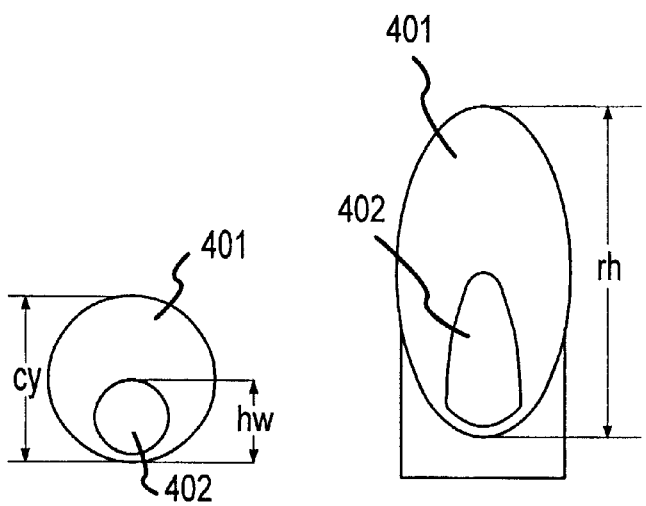
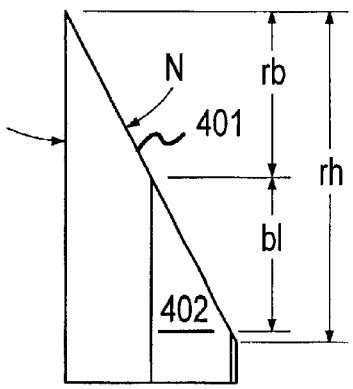
FIG.12  FIG.13  FIG.14
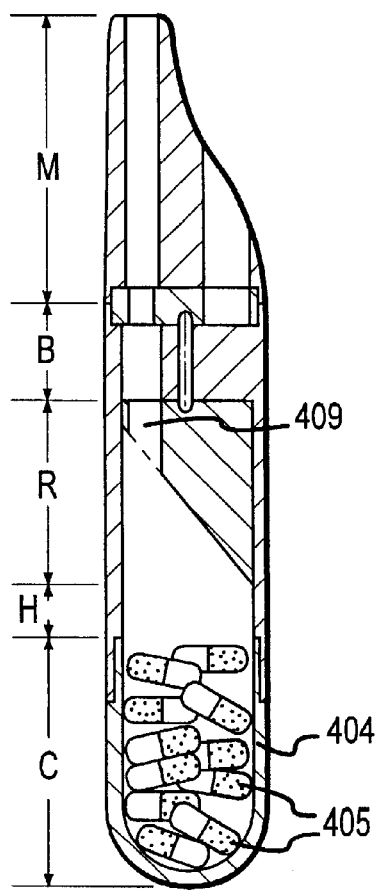
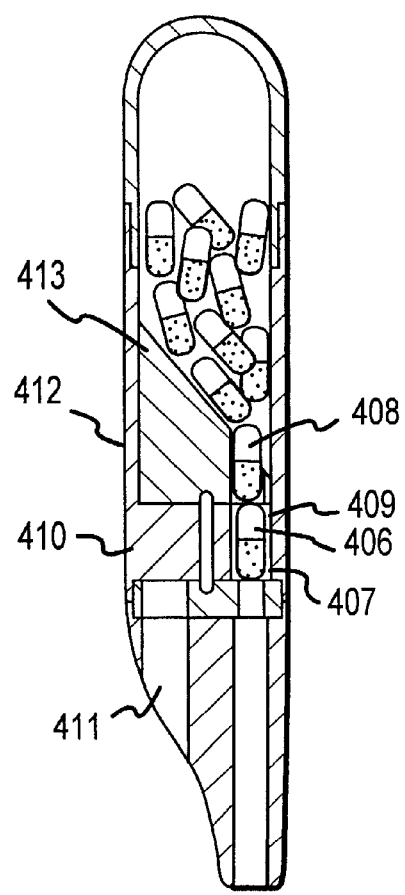
FIG.15  FIG.16

PARTICULATE DRUG-CONTAINING PRODUCTS AND METHOD OF MANUFACTURE

CROSS-REFERENCE TO RELATED APPLICATION

This application is a continuation-in-part of U.S. patent application Ser. No. 09/604,786 filed Jun. 26, 2000, now abandoned which is a continuation-in-part of U.S. patent application Ser. No. 09/469,733, filed Dec. 21, 1999, the entire contents of both of which are incorporated herein as if set forth herein in full.

FIELD OF THE INVENTION

The invention involves particulate products including an active drug useful for pulmonary delivery applications, manufacture of particles of the product using compressed anti-solvent precipitation, and inhalers actuatable to aerosolize the product and produce aerosols including the active drug. In one aspect, the particles are multi-component particles including the active drug and a biocompatible polymer useful for sustained release applications.

BACKGROUND OF THE INVENTION

Recently, there has been significant interest in pulmonary delivery of a variety of drugs to subjects via inhalation of aerosolized drug powders.

One important consideration for pulmonary delivery is that small particles in a narrow range of aerodynamic diameters of from about 1 micron to about 5 microns appear to be most effective for deposition in the lungs in a manner to contribute to drug delivery. Larger particles tend to become lodged in the throat during inhalation and smaller particles tend to be exhaled without depositing in the lungs. Because it is difficult to manufacture powder batches restricted to the desired particle size, significant losses of drugs are often experienced during administration to a subject, due to the presence of large quantities of excessively large and/or excessively small particles. Another important consideration is that handling the drug micro-powders during dose measurement and packaging is difficult, because of the small size and often cohesive nature of the particles. Significant quantities of powder can be lost during these handling operations. Significant powder losses can also occur during aerosolization of the powder to produce an aerosol for inhalation by a subject. For example, a dry powder inhaler is typically used to aerosolize a dry powder for inhalation. Significant powder losses in a dry powder inhaler can be caused by poor dispersability of the powder due to interparticulate cohesive forces and by particles coating interior surfaces of the inhaler. The cumulative losses can be large due to combined losses from powder handling, aerosolization and less than optimum particle size and size distribution characteristics. Moreover, if the powder has poor dispersability characteristics, then the aerosol may include a significant quantity of large aggregates that are too large for effective deposition in the lungs. The result is that often only a small percentage of a batch of powder originally manufactured for pulmonary delivery is ultimately delivered to the lungs of a subject. Some of these losses can be reduced through careful design of handling operations and careful design of inhalers to promote satisfactory aerosolization. Losses could further be reduced, however, through manufacture of powders having improved particle size and size distribution characteristics, improved flowability for ease of handling and/or improved dispersability for ease of aerosolization.

One drug that has received considerable attention for pulmonary delivery is insulin. Techniques that have been proposed for preparing insulin powders for pulmonary delivery include spray drying, solvent extraction and jet milling of lyophilized insulin. One problem with spray drying, however, is that the insulin is subjected to high temperatures, which can significantly degrade the insulin and may impair its activity. With solvent extraction techniques, there are often significant problems associated with contamination of powders by residual solvents and surfactants used during the manufacturing operation. The presence of these residual contaminants is undesirable. Jet milling can damage the biological activity of the insulin. Also, the characteristics of powders produced by spray drying, solvent extraction and jet milling could be improved to reduce losses during powder handling and aerosolization and to improve delivery of the aerosolized powder to a subject's lungs.

Another method that has been proposed for manufacturing insulin powders is to precipitate insulin from solution by contacting the solution with an anti-solvent fluid under supercritical conditions. Some references discussing supercritical anti-solvent precipitation of insulin include: Yeo, Sang-Do, et al., "Formation of Microparticulate Protein Powders Using a Supercritical Fluid Antisolvent," Biotechnology and Bioengineering, Vol. 41, pp. 341–346 (1993); Yeo, Sang-Do, et al., "Secondary Structure Characterization of Microparticulate Insulin Powders," J. Pharmaceutical Sciences, Vol. 83, No. 12, pp. 1651–1656 (1994); Winters, Michael A., et al., "Precipitation of Proteins in Supercritical Carbon Dioxide," J. Pharmaceutical Sciences, Vol. 85, No. 6, pp. 586–594 (1996); Winters, Michael A., et al., "Long-Term and High-Temperature Storage of Supercritically-Processed Microparticulate Protein Powders," Pharmaceutical Research, Vol. 14, No. 10, pp. 1370–1378 (1997); and European Patent No. 0 542 314.

The supercritical anti-solvent precipitation technique has the advantages of producing insulin powders with very little, if any, residual solvent contamination without subjecting the insulin to a high temperature. The noted references, however, are primarily focused on supercritical anti-solvent precipitation of insulin powders for use in applications other than pulmonary delivery, such as subcutaneous applications, and do not discuss processing techniques specifically designed to produce powders with characteristics that are advantageous for pulmonary delivery applications.

Furthermore, the same problems that exist for the manufacture of insulin powder for pulmonary delivery applications also apply to a wide range of other drugs.

Also, for a powder to be practically useful for pulmonary delivery applications, it is important that the powder be aerosolizable in an efficient manner, without excessive loss of material. This has been a significant problem in providing products for many pulmonary delivery applications. Additionally, the problem with powder aerosolization is often compounded because a given powder may work well with one inhaler design and not with another, and it is important to find a good match between characteristics of the powder and the inhaler.

There is a significant need for improved techniques to prepare insulin and other drug-containing powders for pulmonary delivery applications and for powder/inhaler combinations that efficiently aerosolize powders for pulmonary deliver.

SUMMARY OF THE INVENTION

With the present invention, it has been found that drug-containing powders often having improved characteristics for pulmonary delivery applications are manufacturable by compressed anti-solvent precipitation when the drug is processed in a feed solution including the drug in a cosolvent system including two or more mutually soluble organic solvents. Surprisingly, it has further been found that the powders so manufactured can be efficiently aerosolized in a variety of inhalers, with a particularly preferred inhaler involving fluidization of the powder in a chamber under certain conditions that effectively disaggregate large particle units manufacturable by the present invention. It has further been surprisingly found that the aerosolizability of powders of the present invention can be modified through modification of the geometry of the precipitation chamber used during the compressed anti-solvent manufacture. In particular, powders having tap densities in a desirable range of from about 0.1 to about 0.5 g/cm$^3$ can be prepared using a shorter precipitation chamber, while using a longer chamber tends to promote lower tap density powders. The higher tap density powders are particularly preferred for use with certain dry powder inhalers.

In one aspect the present invention provides a method of making drug-containing powders in which a feed solution including the drug in such a cosolvent system is contacted with a compressed anti-solvent fluid, typically compressed carbon dioxide in a near critical or supercritical state, to precipitate drug-containing particles that are then separated from the anti-solvent fluid. The cosolvent system includes at least a first organic solvent and a second organic solvent, although additional organic solvents may be included as desired for a particular application. The first organic solvent in the cosolvent system is typically a significantly better solvent for the drug and the second organic solvent typically significantly enhances processing to promote preparation of high quality powders for pulmonary delivery applications. As a further possible refinement, it is typically preferred that the cosolvent system include less than about 50% by weight of the first organic solvent.

It has been found that prior supercritical anti-solvent techniques that describe use of a single solvent system for drug manufacture, typically either DMSO or DMFA as the sole solvent, do not produce powders with sufficiently good flowability or dispersability characteristics to be advantageous for pulmonary delivery. Processing according to the method of the present invention, however, often results in significantly enhanced flowability and/or dispersability of the powders. As a possible refinement on the present invention, it has further been found that the cosolvent system should preferably be substantially organic in nature, meaning that it should preferably be substantially free of water. Although at first blush it might seem that the presence of some water in the cosolvent system would stabilize the drug during processing, it has been found that the presence of water in the cosolvent system can often be highly detrimental to flowability and/or dispersability characteristics of the manufactured powder.

With the manufacture method of the present invention, the specific mutually soluble organic solvents preferred for inclusion in the cosolvent system will depend upon the specific composition and/or other characteristics of drug-containing particles to be manufactured. In one embodiment, substantially pure drug particles are manufactured. In that case, examples of some preferred cosolvent systems include DMSO as the first organic solvent and a lower alcohol, such as methanol, ethanol or isopropanol (also referred to herein as isopropyl alcohol), as the second organic solvent. In another embodiment, multi-component particles are manufactured that include both drug and a biocompatible polymer as an exipient for sustained release of drug. To manufacture such multi-component particles for sustained release, examples of some preferred cosolvent systems include a lower alcohol, such as methanol, ethanol or isopropanol, as the first organic solvent and methylene chloride as the second organic solvent. When methanol, ethanol or isopropanol is used as the first organic solvent, the first organic solvent will typically be acidified with addition of a small quantity of acid, such as HCl.

In another aspect, the present invention provides a drug-containing powder useful for pulmonary delivery of drug. These powders are manufacturable by the method of the present invention and typically have desirable flowability and/or dispersability characteristics for pulmonary delivery, and typically can also be manufactured with high tap densities desirable for use in inhalers for pulmonary delivery. In one embodiment, the powder includes substantially pure drug. In another embodiment, the powder includes multi-component particles with drug and a biocompatible polymer for sustained release of drug. Particularly noteworthy with respect to the multi-component powders is that they can be made to have a high degree of drug encapsulation, which promotes a prolonged release of drug following administration to a subject. Although the degree of encapsulation can be varied depending upon the specific requirements for a particular application, in most cases, the degree of drug encapsulation will be at least 30%, and will frequently be much higher. For many applications, the degree of drug encapsulation will be 70% or more. The degree of drug encapsulation provides an indication as to the sustained release characteristics of a powder, with a higher degree of drug encapsulation generally corresponding with a lower level of drug burst. A high degree of drug encapsulation is often achievable with the present invention even when the drug load in the multi-component particles is high. For example, high degrees of drug encapsulation have been achieved with drug loading of 25 weight percent, and even 50 weight percent drug in the powder.

In one aspect, the present invention provides a powder having desirable characteristics for use in pulmonary delivery applications. In one embodiment, the powder, as manufactured, is largely in the form of large particles, having an envelope diameter typically larger than about 10 microns, frequently larger than 25 millions, and often much larger. Surprisingly, it has been found that these larger particles are effectively broken into smaller particles during aerosolization for pulmonary delivery, so that the powders of the present invention can be aerosolized to produce aerosols of particles having a mass media aerodynamic diameter of smaller than about 6 microns, and typically even smaller.

In another aspect, the invention provides a method of generating an aerosol for pulmonary delivery applications. Powders of the present invention are aerosolized by an inhaler to break apart larger particle units in the powder into smaller particles to produce an aerosol including particles having a mass median aerodynamic diameter of smaller than about 6 microns, and typically even smaller.

In yet another aspect, the present invention provides a packaged powder product including powder of the present invention contained in a container that is receivable by and operable with an inhaler, typically a dry powder inhaler, so that when the inhaler is actuated the powder is removed from the container and aerosolized to produce an aerosol including dispersed drug particles for inhalation by a subject for pulmonary delivery. In one embodiment, the container includes a plurality of compartments, each including a drug-containing powder batch including a unit dose of drug, such that each successive actuation of the inhaler aerosolizes a different powder batch to provide an aerosol with a single dose of drug when inhaled by a subject. In another embodiment, the container is a capsule including a single dose of the drug, which capsule is capable of being processed by an inhaler to aerosolize powder from the capsule for pulmonary delivery applications.

These and other aspects of the present invention will be more fully appreciated based on the detailed disclosure provided below.

BRIEF DESCRIPTION OF THE DRAWINGS

FIG. 1 is a block flow diagram of one embodiment of compressed anti-solvent processing of the present invention for manufacture of drug-containing powders.

FIG. 2 is a plot showing blood plasma drug concentration vs time following administration of multi-component particles of the present invention to a rabbit as described in Example 3.

FIG. 3 is a photomicrograph showing an aggregate structure from a drug-containing powder of the present invention.

FIG. 4 is a longitudinal section of one embodiment of an inhaler device useful with the present invention.

FIG. 5 is a longitudinal section of another embodiment of an inhaler device useful with the present invention.

FIG. 6 is a longitudinal section of another embodiment of an inhaler device useful with the present invention.

FIG. 7 is a front elevation of an embodiment of a capsule used with one inhaler device useful with the present invention.

FIG. 8 is a rear elevation of the capsule of FIG. 7.

FIG. 9 is a side elevation of another embodiment of an inhaler device useful with the present invention.

FIG. 10 is an exploded view of the components of the inhaler device of FIG. 9 (also with a cap.

FIG. 11 is a detail section along the axis of bore 220, showing a capsule positioned in the device of FIG. 10.

FIGS. 12, 13 and 14 are top, front and side views of part of another embodiment of an inhaler device useful with the present invention.

FIG. 15 is a cross-sectional view showing the sides of an inhaler described in U.S. application Ser. No. 08/382,425, U.S. Pat. No. 5,589,487 incorporating an inhaler device useful with the present invention, the entire contents of U.S. application Ser. No. 08/382,425 U.S. Pat No. 5,589,487 being incorporated herein in its entirety as if set forth herein in full.

FIG. 16 is a side view of the inhaler of FIG. 15.

FIG. 17 is a schematic of one embodiment of a precipitation chamber useful with the present invention.

FIG. 18 is a photomicrograph of insulin powder prepared according to Example 4.

FIG. 19 is a photomicrograph of a powder of 50 wt. % glucagon and 50 wt. % dipalmitoylphosphatidylcholine prepared according to Example 4.

FIG. 20 is a photomicrograph of a powder of 67 wt. % glucagon and 33 wt. % dipalmitoylphosphatidylcholine prepared according to Example 4.

DETAILED DESCRIPTION OF THE INVENTION

In one aspect, the present invention involves an anti-solvent precipitation process for manufacturing drug-containing powders designed specifically for pulmonary delivery applications. It has been found that powders having advantageous properties for pulmonary delivery applications can be prepared by contacting a liquid feed containing one or more drug with a compressed anti-solvent fluid, wherein the liquid feed includes a certain type of cosolvent system. It has further been found that the geometry of the precipitation apparatus can be modified to beneficially modify powder characteristics, and specifically to improve tap density of the powder for pulmonary delivery applications.

Referring to FIG. 1, a simplified process flow diagram shows general processing involved with one embodiment of the anti-solvent precipitation method of the present invention for manufacturing drug-containing powders. As shown in FIG. 1, a feed solution 102 including at least one drug, and a compressed anti-solvent feed 104 are contacted in a contacting step 106 to form drug-containing particles as the anti-solvent feed 104 invades and expands the feed solution 102. The resulting mixture 108 of process fluids and drug-containing particles is then subjected to a solid/liquid separation 110 to recover a drug-containing particulate product 112. Process fluid 114 remaining after the separation step 110 includes anti-solvent fluid from the anti-solvent feed 104 and solvents removed from the feed solution 102 during the contacting step 106. The contacting step 106 and the separation step 110 are shown as two separate steps, but it will be appreciated that these steps could be conducted as separate operations in separate process apparatus, or could be conducted as a combined operation in a single process apparatus.

The compressed anti-solvent feed 104 includes a compressed anti-solvent fluid having a strong solvating power for solvents in the feed solution 102, and in which the drug should be no more than slightly soluble. Any material or combination of materials may be used as the anti-solvent fluid that is suitable for processing under the specific operating conditions contemplated. Preferably, the drug being processed should be essentially insoluble in the compressed anti-solvent fluid. Nonlimiting examples of materials that may be used as the compressed anti-solvent fluid include one or more of carbon dioxide, ethane, ethylene, nitrous oxide, fluoroform ($CHF_3$), dimethyl ether, propane, butane, isobutane, propylene, chlorotrifluoromethane ($CClF_3$), sulfur hexafluoride ($SF_6$), bromotrifluoromethane ($CBrF_3$), chlorodifluoromethane ($CHClF_2$), hexafluoroethane, carbon tetrafluoride, monofluoromethane, 1,1-difluoroethylene, ammonia, nitrogen, argon and combinations of the foregoing. Particularly preferred for use as the compressed anti-solvent fluid is carbon dioxide. Also, it is preferred that the anti-solvent feed 104 consist essentially of the compressed anti-solvent fluid.

The anti-solvent feed 104 is typically in a near critical or supercritical state when contacted with the feed solution 102 during the contacting step 106, and the contacting step 106 is conducted in a pressurized vessel, at the desired temperature and pressure. The contacting step 106 is typically conducted at a reduced temperature of larger than about 0.90, and preferably larger than about 0.95, calculated relative to the critical temperature of the anti-solvent fluid. Although the temperature during the contacting step 106 may be as high as desired, so long as not significantly detrimental to the drug, the contacting step 106 will typically be conducted at a reduced temperature in a range having an upper limit of about 1.10, and more preferably about 1.05, as calculated relative to the critical temperature of the anti-solvent fluid. The reduced temperature of a fluid is the ratio of the temperature of the fluid to the critical temperature of the fluid, with the temperatures in the ratio being expressed in K. For carbon dioxide, the critical temperature is 31° C. (304 K). Therefore, for carbon dioxide, a reduced temperature in a preferred range of from about 0.95 to about 1.05 translates to a preferred operating temperature range during the contacting step 106 of from about 16° C. (188 K) to about 46° C. (319 K). Also, the contacting step 106 is typically conducted at a reduced pressure of larger than about 0.5, preferably larger than about 0.8, and more preferably larger than about 0.9, calculated relative to the critical pressure of the anti-solvent fluid. Although the pressure during the contacting step 106 may be as high as desired, so long as not significantly detrimental to the drug, the contacting step will typically be conducted at a reduced pressure in a range having an upper limit of about 2, and preferably about 1.5, relative to the critical pressure of the anti-solvent fluid. The reduced pressure of a fluid is the ratio of the pressure of the fluid to the critical pressure of the fluid. For carbon dioxide, the critical pressure is 72.9 atmospheres. Therefore, for carbon dioxide, a reduced pressure in a preferred range of from about 0.9 to about 1.5 translates to an operating pressure range during the contacting step 106 of from about 66 atmospheres to about 109 atmospheres. In many instances, the contacting step will be performed under supercritical conditions, meaning that the reduced temperature for the anti-solvent fluid is greater than 1 (in which case the reduced pressure will also necessarily be greater than 1).

The separation step 110 may involve any suitable technique for separating the drug-containing particles from process fluids to produce the drug-containing particulate product 112 and the process fluids 114. Examples of suitable separation techniques include sedimentation, filtration and centrifuging. Filtration is a generally preferred technique for the separation step 110.

As noted previously, with the manufacture method of the present invention, the feed solution 102 comprises a cosolvent system including the drug. The drug will typically be in the form of a true solution in the cosolvent system. In some applications, however, some or all of the drug may be suspended in a colloidal state in the cosolvent system. Therefore, as described herein, the "feed solution" includes the situation when some or all of the drug is dissolved in the cosolvent system in a true solution (i.e., dispersion of drug in the cosolvent system at a molecular level) and includes the situation when some or all of the drug is in the state of a "colloidal solution" (i.e., dispersion of the colloidal-sized drug domains suspended in and dispersed throughout the cosolvent system). Furthermore, when it is said herein that drug-containing particles are "precipitated," such precipitation includes the situation when some or all of the drug, or some or all of some other component to be included in the particles, comes out of a true solution to form the particles, as well as the situation when the cosolvent system is removed from a colloidal suspension of drug, to form drug-containing particles no longer trapped as a dispersed colloidal phase in the cosolvent system.

The drug processible according to the present invention may be any drug that is no more than slightly soluble in, and preferably substantially insoluable in, the anti-solvent fluid. Examples of drugs for use with the present invention include proteins, peptides, genetic materials and small molecule drugs. The drug may be dissolved in the cosolvent system or may be suspended as small particulates in the cosolvent system. If desired, more than one drug may be dissolved and/or suspended in the cosolvent system.

According to the present invention, the cosolvent system includes two or more different organic solvents that are mutually soluble in the proportions used and at the temperature and pressure conditions existing during the contacting step 106, and that are also preferably mutually soluble at ambient conditions of temperature and pressure. It has been found that manufacture using the cosolvent system according to the invention often produces drug-containing powders that have improved characteristics for use in pulmonary delivery applications. The specific solvents used in the cosolvent system will depend upon the particular application, as discussed more fully below. For most applications, however, a first organic solvent will be a significantly better solvent for drug and another organic solvent will be a significantly worse solvent for drug. The first organic solvent and the second organic solvent may be present in the cosolvent system in any proportion suitable for processing under the desired conditions. For most applications, the cosolvent system is preferably richer in the second organic solvent than in the first organic solvent. When the drug is to be dissolved in the cosolvent system to form a true solution, then the proportion of the first organic solvent must be large enough to solubilize the drug at a sufficiently high concentration for processing into the desired drug-containing particles. However, when the drug is in the form of a colloidal suspension in the cosolvent system, then the proportion of the first organic solvent will be lower than that required for a true solution. Typically, the weight ratio of the second organic solvent to the first organic solvent in the cosolvent system is in a range having a lower limit of about 10:90, preferably about 30:70 and more preferably about 50:50 and having an upper limit of about 99:1, preferably about 90:10 and more preferably about 80:20. Particularly preferred is for the weight ratio of the second organic solvent to the first organic solvent to be in a range of from about 50:50 to about 80:20. The concentration of drug dissolved and/or suspended in the cosolvent system will depend upon the specific powder to be manufactured, but will typically be in a range of from about 0.1 to about 5 mg of drug per milliliter of the cosolvent system, with concentrations of smaller than about 3 mg of drug per milliliter of the cosolvent system being generally preferred for most applications.

An important consideration for selecting solvents for inclusion in the cosolvent system is the composition of the particular drug-containing powder to be made. In that regard the drug-containing powder may include substantially only drug, or may include one or more other components in addition to drug. A preferred multi-component powder includes the drug together with a biocompatible polymer, preferably in a form that significantly prolongs release of the drug following pulmonary delivery to a subject.

In one preferred embodiment of the manufacture process of the present invention, the drug-containing powder includes substantially only the drug. When preparing single component powders of substantially pure drug, the cosolvent system will typically include at least a first organic solvent that is a significantly better solvent for the drug and a second organic solvent that is a significantly worse solvent for the drug, and with the second organic solvent preferably being more readily extractable by the anti-solvent feed 104 than the first organic solvent. The first organic solvent may be any solvent in which drug is sufficiently soluble and that is at least reasonably extractable by the anti-solvent feed 104. Examples of organic solvents for use as the first organic solvent in this embodiment include dimethyl sulfoxide (DMSO), dimethyl formamide (DMFA) and lower alcohols (especially $C_1$–$C_5$ alkanols) such as acidified methanol and ethanol. DMSO is particularly preferred for use as the first organic solvent to make substantially pure drug powders. When using a lower alcohol, such as methanol or ethanol, or when using DMFA as the first organic solvent, it is sometimes desirable to add a small amount of acid, such as hydrochloric acid, to the first organic solvent to enhance the solubility of drug, but it is better to avoid this if possible.

When making substantially pure drug powders, the second organic solvent may be any organic solvent that is miscible with the first organic solvent under the operating conditions of the contracting step 106 and that is readily extractable by the anti-solvent feed 104. Typically, organic solvents that have a higher volatility are more readily extractable by the anti-solvent feed 104. Therefore, the second organic solvent will typically be a more volatile solvent than the first organic solvent. Examples of groups of organic liquids that may be used as the second organic solvent include various alcohols, ketones, aldehydes, nitrites, and halogenated hydrocarbons, and particularly lower molecular weight members of these groups that are readily extractable by the anti-solvent feed 104. For example, preferred alcohols are C1–C5 alkanols, which will typically be monohydric, and may be primary, secondary or tertiary alcohols. Examples of particularly preferred alcohols include methanol, ethanol, propanols (including isopropanol and n-propanol), butanols and pentanols, with the most preferred alcohols being methanol, ethanol and isopropanol. Also for example, one preferred halogenated hydrocarbon is chloroform.

It should be noted that the cosolvent system may include more than one mutually soluble solvent. For example, the cosolvent system could include more than one solvent from the list of exemplary first organic solvents and/or may include more than one solvent from the list of exemplary second organic solvents. For example, one preferred cosolvent system for making powders of some drugs, such as glucagon and insulin, includes 50% DMSO, 40% chloroform and 10% methanol, by weight. Moreover, the cosolvent system may include one or more mutually soluble solvents other than the first organic solvent and the second organic solvent, to the extent that the additional solvent is not inconsistent with operation of the anti-solvent precipitation operation Solvents such as DMSO and DMFA, which are useful as the first organic solvent with the present invention, have previously been identified in the literature as solvents in which drug may be dissolved for anti-solvent precipitation to prepare drug powders. It has been found with the present invention, however, that the use of either DMSO or DMFA alone is typically problematic. For example, solutions of drug in either DMSO or DMFA tend to be very viscous and difficult to process. Furthermore, drug powders prepared using only DMSO or DMFA as a solvent tend to not be free flowing, and are often sticky and therefore difficult to handle and disperse. With the present invention, however, it is been found that the problems associated with the use of only DMSO or DMFA can largely be avoided by using the cosolvent system, resulting in feed solutions that are easier to process and manufactured drug-containing powders that are more likely to be free flowing. Free-flowing powers are particularly preferred for use in pulmonary delivery applications, because free flowing powders tend to be easier to handle, to be easier to disperse during aerosolization, and to produce higher quality aerosols for delivery of drug to a subject's lungs.

In another preferred embodiment of the manufacture process of the present invention, multi-component powders are prepared including drug and a biocompatible polymer. Other components may also be included in these multi-component powders, if desired. Multi-component powders including drug and a biocompatible polymer are typically intended for sustained release of drug when administered by pulmonary delivery. A significant aspect of this embodiment of the present invention is that the multi-component powders may be made with a high degree of encapsulation of the drug by the biocompatible polymer. This result is particularly surprising, because previous experience of the inventors has indicated that it is very difficult to obtain a high degree of encapsulation of the drug.

In this embodiment, both the drug and the biocompatible polymer are typically included in the cosolvent system. Some or all of the drug and/or the biocompatible polymer can be dissolved in the cosolvent system, to form a true solution, or may be in the form of a colloidal dispersion in the cosolvent system. Preferably, however, at least the biocompatible polymer will be dissolved in the cosolvent system. The cosolvent system will typically include a first organic solvent that is a better solvent for drug and a second organic solvent that is a better solvent for the biocompatible polymer. Examples of biocompatible polymers useful with the present invention include repeating units representative of polymerizing at least one of the following: an alphahydroxycarboxylic acid, a cyclic diester of an alphahydroxycarboxylic acid, a dioxanone, a lactone, a cyclic carbonate, a cyclic oxalate, an epoxide, and a glycol. Preferred biocompatible polymers comprise at least some repeating units representative of polymerizing at least one of lactic acid, glycolic acid, lactide, glycolide, ethylene oxide and ethylene glycol. Other examples of biocompatible polymers include poloxamers (polyethoxy-polypropoxy triblock copolymers), polyanhydrides, and phosphatriazenes. Polyanhydrides are copolymers typically of a bis(p-carboxyphenoxy) alkane (typically $C_3$–$C_6$ alkanes) and dicarboxylic acid (such as sebacic acid or fumaric acid). Phosphatriazenes are copolymers typically made by reacting a polychlorophosphazene with various nucleophiles in various ratios. Specific examples of phosphotriazenes include poly(p-methylphenoxy-imidazole) phosphozene and poly(ethylglycinato)(p-methylphenoxy) phosphazene. In most cases the biocompatible polymer is hydrophobic, although in some instances the biocompatible polymer may be hydrophilic, such as for example in the case of polyethylene glycol. The biocompatible polymer may be of any desired molecular weight that is soluble in the cosolvent system. Generally preferred molecular weights are in a range of from about 2 kDa to about 300 kDa, and preferably of from about 20 kDa to about 150 kDa. One class of preferred biocompatible polymers for use with the invention is biodegradable polymers, meaning that the matrix of the polymer will degrade over time after administration to a subject. Hydrolytic degradation is a common degradation mechanism for preferred biocompatible polymers. The biocompatible polymer need not be biodegradable, however. For example, polyethylene glycol and poloxamers are not biodegradable, but are excreted or exhaled by the host largely intact.

A particularly preferred biocompatible polymer for use with the present invention is poly(lactic acid). As used herein, poly(lactic acid) means polymers having repeating units

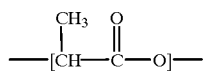

regardless of the monomer from which the repeating units are derived. For example, as used herein, poly(lactic acid) includes polymers made by condensation polymerization of lactic acid as a monomer as well as by ring-opening polymerization of lactide as a monomer. Furthermore, the poly (lactic acid) may be poly (L-lactic acid), poly (D-lactic acid) or poly (D,L-lactic acid), although poly(D-lactic acid) and poly(L-lactic acid) are generally preferred. Although any desired molecular weight of poly(lactic acid) may be used that is soluble in the cosolvent system, preferred molecular weights for use with the present invention are in a range of from about 2 kDa to about 300 kDa, with molecular weights of from about 20 kDa to about 150 kDa being more preferred.

The biocompatible polymer and the drug may be included in any desired proportions. Typically, the weight ratio of the drug to the biocompatible polymer will be in a range of having a lower limit of about 1:99, preferably about 5:95 and more preferably about 10:90 and having an upper limit of about 99:1, preferably about 65:35, more preferably about 50:50 and even more preferably about 35:65. Particularly preferred for most applications is a weight ratio range of from about 10:90 to about 35:65.

As noted previously, when making the multi-component particles including a biocompatible polymer, the first organic solvent is typically a better solvent for the drug and the second organic solvent is typically a better solvent for the biocompatible polymer. Furthermore, the first organic solvent is typically a poor solvent for the biocompatible polymer and the second organic solvent is typically a poor solvent for drug. Also, because the biocompatible polymer is typically hydrophobic, the second organic solvent is typically a non-polar solvent. Conversely, when the drug is hydrophilic the first organic solvent is typically a polar solvent. The solubility of drug in the first organic solvent is often at least an order of magnitude larger than the solubility of the biocompatible polymer in the first organic solvent, and the solubility of the biocompatible polymer in the second organic solvent is often at least an order of magnitude larger than the solubility of drug in the second organic solvent. Examples of solvents useful as the first organic solvent for use in the manufacture of many drugs include DMSO, DMFA, alcohols, and more preferred are lower molecular weight alcohols, and particularly C1–C5 alkanols. Particularly preferred are methanol, ethanol, propanols (including n-propanol and iso-propanol), butanols, and pentanols; with methanol, ethanol and iso-propanol being even more preferred. When DMFA or alcohols are used as the first organic solvent, they will often be acidified, such as with a small quantity of HCl, to improve the solubility of the drug in the cosolvent system.

Examples of solvents useful as the second organic solvent when making multi-component particles include methylene chloride, formaldehyde, dioxolane, chloroform, benzene, ethyl ether, toluene, xylene, 1,3-dioxane and tetrahydrofuran (THF). Certain second organic solvents will generally be more preferred for use with different biocompatible polymers. For example, preferred second organic solvents include: 1) for poloxamers—methylene chloride, chloroform, THF and 1,3-dioxane; 2) for polyanhydrides—methylene chloride, chloroform, benzene, ethyl ether, toluene, xylene, THF and 1,3-dioxane; 3) for phosphatriazenes—THF, chloroform, 1,3-dioxane and methylene chloride; and 4) for poly(lactic acids)—methylene chloride, formaldehyde, dioxolane and chloroform. Especially preferred as the second organic solvent for most applications, and especially for use with poly(lactic acids), is methylene chloride.

As noted above, the cosolvent system may include one or more solvents in addition to the first organic solvent and the second organic solvent. As one example, the cosolvent system could include DMSO and a C1–C5 alkanol (which together solubilize the drug) and methylene chloride (to solubilize the biocompatible polymer). Furthermore, the cosolvent system may include more than one biocompatible polymer, with the cosolvent system being chosen to solubilize all of the different biocompatible polymers being used.

In some instances, when it is necessary to improve the solubility of the drug in the first organic solvent, particularly in lower alcohols, a small amount of acid, such as hydrochloric acid can be added to aid solubility, but this practice is not preferred. Instead, it is preferred to find a mixture of solvents be used that does not require the addition of acid. When used, however, the acid should typically be at only low concentrations. Typically, the concentration of such and acid when used in the cosolvent system should be smaller than about 10 mM, with a range of from about 1 mM about 3 mM being generally more preferred for most situations.

A further enhancement to the manufacture process when making multi-component particles including the biocompatible polymer is to prepare a first solution including the drug and at least the first organic solvent and a second solution including the biocompatible polymer and at least the second organic solvent, and to mix the first solution and the second solution during preparation of the feed solution 102. Also, it is further preferred that the second solution be added to the first solution, to prevent precipitation of the drug, which is often more susceptible to coming out of solution if the first solution is added to the second solution. When the acid is to be included in the feed solution 102, it is preferred that the first solution include the acid prior to mixing with the second solution.

In one embodiment, the drug is in the cosolvent system in the form of a colloidal suspension when the feed solution 102 is contacted with the anti-solvent feed 104 (referring again to FIG. 1). The biocompatible polymer, however, will still typically be dissolved in the cosolvent system in the form of a true solution. This will often be the case, for example, when the first organic solvent is a lower alcohol and the acid addition is extremely small, or when an acid is not used at all. It has been found with the present invention that processing the drug into the form of a colloidal suspension in the cosolvent system produces high quality powders, and permits the use of lower concentrations of the acid or an elimination of the acid altogether in some instances, which is generally preferred. Another example of a cosolvent system where the drug may be in the form of a colloidal suspension in the cosolvent system is when the first organic solvent is DMSO and the second organic solvent is methylene chloride, especially when the proportion of DMSO is relatively small. The processing of drug in the form of a colloidal suspension is an important and advantageous aspect of the present invention.

Another possible enhancement with the manufacture process, whether making single-component or multi-component particles, is to maintain the concentration of dissolved drug in the cosolvent system at a relatively low level. Frequently, it is desirable to maintain the concentration of drug in the cosolvent system at smaller than about 3 mg (and often in a range of from about 0.3 to about 3 mg) of drug per milliliter of the cosolvent system. When making single component drug particles, a preferred range of drug concentration is frequently from about 0.5 to about 3 mg (more preferably from about 0.5 to about 2 mg) of drug per milliliter of the cosolvent system. When making multi-component particles, a preferred range of drug concentration is often from about 0.3 to about 1 mg (more preferably from about 0.4 to about 0.8 mg) of drug per milliliter of the cosolvent system. Operating according to the present invention using a cosolvent system with a relatively low concentration of dissolved drug has been found to advantageously promote the precipitation of drug powders suitable for use in pulmonary delivery applications. Furthermore, the process of the present invention lends itself to scale-up. For example, with the process of the present invention, it is typically possible to introduce the feed solution into the compressed anti-solvent without requiring the introduction to be accomplished using a small diameter capillary or orifice. For example, some prior art processes for compressed anti-solvent precipitation of drug operated at high drug concentrations in the feed solution and/or introduced the drug into the compressed anti-solvent fluid through a very small orifice, such as 50 microns or smaller. With the use of the present invention, by processing drug at a relatively low concentration and using the cosolvent system, the feed solution 102 may be introduced into the anti-solvent fluid through a significantly larger opening while maintaining a high quality powder product. This is important because with large orifices, precipitation would not be expected to proceed as quickly as when using a small orifice, and powder quality could, accordingly, suffer. Therefore, the ability to introduce the feed solution 102 through a larger opening with the present invention while maintaining a high quality product is significant. In one embodiment of the present invention, the feed solution 102 may be introduced into the compressed anti-solvent through an opening having a cross-sectional area available for flow that is larger than about 0.02 square millimeter. In one enhancement, the feed solution 102 is sprayed into the compressed anti-solvent through a spray nozzle having an area available for flow at the outlet of larger than about 1 square millimeter, more preferably larger than about 5 square millimeters and even more preferably larger than about 10 square millimeters.

As another enhancement for the operation of the process of the present invention, also applicable to manufacturers of either single-component or multi-component powders, it has been found that the quality of powders produced may be enhanced by introducing the feed solution 102 into the compressed anti-solvent fluid in a manner to promote more rapid mixing of the feed solution 102 with the compressed anti-solvent fluid, thereby promoting more rapid precipitation from the feed solution 102. In that regard, the feed solution 102 is typically introduced into a significantly larger volume of the flowing anti-solvent feed 104 under the desired conditions of temperature and pressure. For enhanced performance, it is preferred that the feed solution 102 be introduced into the flowing anti-solvent feed 104 so that the feed solution 102, when introduced into the anti-solvent feed 104, has a direction of flow that is in a range of from about 45° to about 180° relative to the direction of flow of the anti-solvent feed 104. More preferred is for the feed solution 102 to have a direction of flow that is in a range of from about 90° to about 180° relative to the direction of flow of the anti-solvent feed 104. Particularly preferred is for the flow of the feed solution 102 to have a direction of flow of about 180° relative to the direction of flow of the anti-solvent feed 104, in which case the feed solution 102 is introduced into the anti-solvent feed 104 in a direction that is directly counter-current to the flow of the anti-solvent feed 104.

Figure 17:
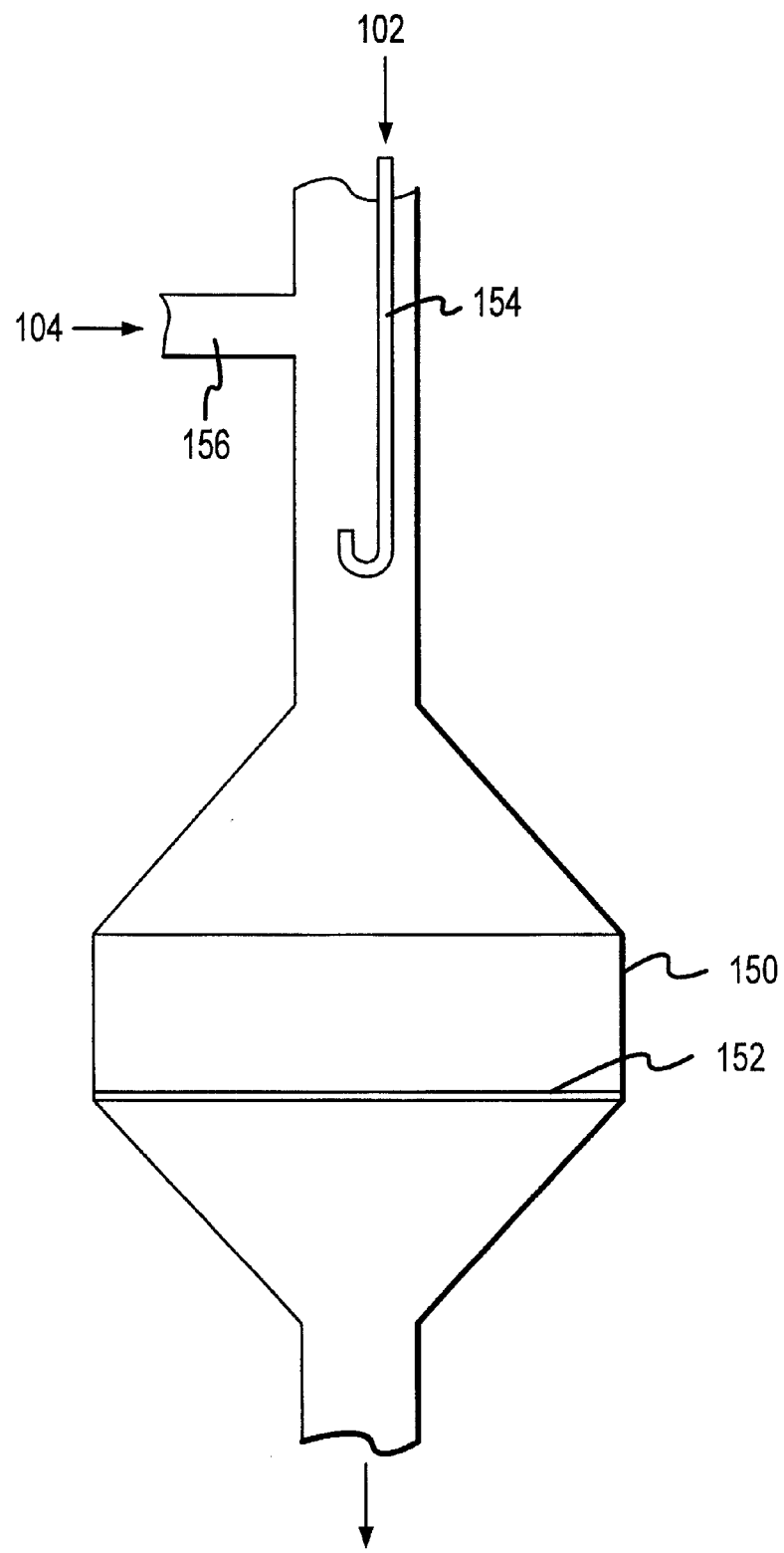

In one embodiment, it has surprisingly been found that the geometry of the anti-solvent precipitation chamber can be modified to advantageously change the characteristics of the powder that is manufactured. In general it has been found that a shorter precipitation chamber is generally preferred to manufacture powders having higher tap densities for use in pulmonary delivery applications. In one preferred embodiment, the precipitation chamber has a diameter (measured perpendicular to flow), that is larger than the height of the chamber (measured parallel to flow). Referring now to FIG. 17, one embodiment of a precipitation chamber is shown. As shown in FIG. 17, a precipitation chamber 150 has disposed therein a filter element 152 on which precipitated powder collects during the anti-solvent precipitation operation. During operation to manufacture powder, the feed solution 102, including at least one drug, is fed through feed tube 154 and the anti-solvent feed 104 is fed through feed tube 156, so that when the direction of flow of the feed solution 102 introduced into the flowing anti-solvent is countercurrent. Occasionally, the chamber is taken off line and the powder removed from the filter.

As noted previously, the cosolvent system may include one or more additional solvents in addition to the first organic solvent and the second organic solvent. Preferably, however, substantially all of the solvents in the cosolvent system are organic solvents that are highly expandable by and soluble in the compressed anti-solvent feed. The cosolvent system should, however, typically not include any significant quantity of water, because water is highly susceptible to phase separation during processing and its presence tends to significantly impair the quality of the powder that is obtained from the process. Although it may appear that the addition of water could be beneficial to help solubilize the drug, it has been found that detrimental aspects of using water during processing outweigh any potential benefits. Although it is preferred that the cosolvent system be substantially free of water, when water is present it should comprise less than about 5 weight percent of the cosolvent system.

In a further aspect, a significant advantage of using the process of the present invention is that it is not necessary to ion pair the drug with amphiphillic materials in order to solubilize the drug for processing to make a high quality powder. Rather, using the cosolvent system with the process of the present invention, no such ion pairing is required to make a high quality drug product. Furthermore, when a drug-containing powder is prepared according to the process of the present invention, it is possible to manufacture a powder of a free flowing nature with good particle characteristics for aerosolization for pulmonary delivery applications and without significant degradation of the drug being observed.

In another aspect, the present invention provides drug-containing powders, particularly suited for use in pulmonary delivery applications, manufacturable by the manufacture method of the present invention as just described. Advantageously, the powders of the present invention are frequently free flowing and highly dispersible. By free flowing, it is meant that the particles of the powder do not tend to strongly adhere to each other or to the surfaces of storage or processing equipment. The result is that the powders are frequently advantageously amenable to processing and handling encountered during measurement and packaging operations without excessive difficulty or excessive powder losses. By highly dispersible, it is meant that the particles tend to be easy to disperse, or separate from each other. A high degree of dispersability is desirable to permit the powder to be easily aerosolized to prepare an aerosol that does not contain a large quantity of excessively large aggregate units. Furthermore, the powders of the present invention typically are aerosolizable to produce an aerosol having dispersed drug-containing particles advantageously having aerodynamic diameters in a range of from about 0.5 micron to about 6 microns or even more preferred in a range of from about 1 micron to about 3 microns. Advantageously, the dispersed drug-containing particles in the aerosol typically will have a mass median aerodynamic diameter of smaller than about 6 microns, and more preferably the mass median aerodynamic diameter will be in a range having a lower limit of preferably about 0.5 micron and more preferably about 1 micron and an upper limit of preferably about 6 microns, more preferably about 5 microns, and even more preferably about 4 microns. Particularly preferred is for the dispersed drug-containing particles in the aerosol to have a mass median aerodynamic diameter in a range of from about 0.5 micron to about 3 microns and even more preferred in a range of from about 1 micron to about 3 microns. As will be appreciated, these stated size characteristics for particles in an aerosol are in reference to the drug-containing particles of the present invention that are present in the aerosol. It is also possible that the aerosol may contain other particles, and that these other particles may be of a larger or smaller size. For example, the aerosol may include larger particles of a bulking agent, such as of lactose or another material now or hereafter known to be used for bulking purposes. This would be the case when a drug-containing powder made by the manufacture method of the present invention is mixed with a bulking agent to form a powder mixture with modified handling characteristics or to cut the concentration of drug in the powder mixture. Such mixed powders are within the scope of the invention, and in such situations, the properties described herein for the drug-containing powders of the present invention refer to the properties of only that portion of such a powder mixture composed of the drug-containing particles of the present invention.

Furthermore, the drug-containing powder of the present invention, as recovered from the manufacture process, is often in the form of relatively large particle units, which may or may not appear to be comprised of smaller primary particles, and which large particles are typically substantially not spherical. For example, with the multi-component particles including drug and a biocompatible polymer are sometimes in the form of large aggregates of smaller primary particles, while particles of pure drug are often in the form of large particulate masses with no discernable primary particle structure. The aggregate units of the multi-component particles may include 100 or more primary particles. In any event, the large particle units typically have a mass average envelope diameter of larger than about 10 microns, more typically larger than about 25 microns, and frequently larger than about 50 microns, with the mass average envelope diameter typically being determinable from analysis of micrographs of a representative powder sample, which analysis may be performed manually or with the use of software analysis techniques. The envelope diameter of a large particle unit is the diameter of the smallest sphere capable of entirely enclosing the entire large particle unit. The primary particles when discernable, however, typically have a mass median diameter of smaller than about 6 microns, more often smaller than about 5 microns and preferably smaller than about 4 microns. The large particle units of the powders of the present invention, whether in aggregate form or a more monolithic form, can typically be broken up, either prior to or during aerosolization, but preferably during aerosolization, to permit production of an aerosol having the desired characteristics, as previously discussed.

In one embodiment, the drug-containing powder of the present invention is made using a co-solvent system for manufacture, as previously described. One problem historically encountered with the manufacture of drug-containing powders is that it has been difficult to produce powders with desirable properties for use in pulmonary delivery applications. It has surprisingly been found, however, that with the present invention, drug-containing powders are manufacturable that frequently include advantageous properties for pulmonary delivery applications, using the co-solvent processing technique previously described. The powders may include the drug in single component particles of substantially pure drug, or may include multi-component particles, such as those including a biocompatible polymer to promote sustained release of the drug, as previously described. Moreover, although the powders of the present invention have been identified as being particularly well suited for use in pulmonary delivery applications, it should be recognized that use of the powders is not so limited. Rather, the powders may be used in any application in which a drug-containing powder is desired, including for example intranasal, injection, oral and dermal applications.

One particularly noteworthy finding is that even though the powders are typically manufactured substantially in the form of large particle units, the powders nevertheless can be aerosolized to produce aerosols with particles suspended in the aerosol being within the desired size range as previously mentioned. Also particularly noteworthy is that the powders are manufacturable having a tap density of larger than about 0.1 gm/cm$^3$, and preferably in a range of from about 0.1 g/cm$^3$ to about 0.5 g/cm$^3$ and more preferably in a range of from about 0.15 g/cm$^3$ to about 0.5 g/cm$^3$. Although performance will vary depending upon the inhaler used, powders having a tap density in the noted ranges are often preferred for use in pulmonary delivery applications because powders having tap densities in those ranges are more efficiently aerosolized by at least some inhalers. This is extremely important, and the ability of the method of the present invention to produce such powders provides a significant advantage.

In one embodiment, the drug-containing powder of the present invention includes multi-component particles having at least the drug and a biocompatible polymer, and having a high degree of drug encapsulation, so that the powder is advantageously suited for sustained release of the drug when administered to a subject. The degree of drug encapsulation of the powder provides an indication as to the degree to which drug will be released from the powder over time relative to a substantially pure drug powder. As used herein, the degree of drug encapsulation of a powder is determined by the following procedure: A 60 milligram sample of the powder in a substantially dry form is immersed in 30 milliliters of a phosphate buffer solution (PBS) containing a small amount of a dispersing agent and maintained at a temperature of approximately 37° C., and the quantity of drug remaining in the powder 15 minutes after immersion is determined. Any suitable PBS solution may be used. A preferred PBS includes 137 mM NaCl, 10.2 mM NaHPO$_4$.7H$_2$O (dibasic sodium phosphate septahydrate), 1.8 mM KH$_2$PO$_4$ (monobasic potassium phosphate), 2.7 mM KCl and 3.1 mM NaN₃ (sodium azide). A small amount of dispersing agent (nonionic surfactant preferred) should be included in the PBS to help keep the powder in a dispersed state during the test. A preferred dispersing agent is Tween™ 20 (polyethylene 20 sorbitan surfactant), or an equivalent nonionic surfactant, which is preferably added in an amount of about 0.2 grams per liter of the PBS, or such other quantity as is required to substantially disperse the particles in the PBS. The Tween™ family of surfactants is well known and such surfactants are available, for example, from Fisher Scientific International, Inc. The degree of drug encapsulation is equal to the percentage of drug remaining in the powder after 15 minutes relative to the quantity of drug originally contained within the powder prior to immersion in the PBS. The PBS may be provided in any convenient container, such in as a 50 milliliter polypropylene centrifuge tube. The powder is immersed in the PBS by adding the drug to the PBS accompanied by thorough mixing to disperse the powder in the PBS. The mixing may be accomplished by vortexing or shaking. The quantity of drug remaining in the drug is determined by first determining the quantity of drug that has dissolved in the PBS during the test and then determining the quantity of drug remaining in the powder by difference. The quantity of drug that has been dissolved in the PBS is determined by taking a sample of the PBS 15 minutes after immersion and measuring the concentration of the drug dissolved in the PBS by a suitable technique, such as by HPLC (high-performance liquid chromatography). A degree of drug encapsulation of 0% indicates that substantially all of the drug dissolves in the PBS during the test and a drug encapsulation of 100% indicates that substantially none of the drug dissolves in the PBS during the test.

Manufacture of the multi-component powder of the present invention with a high degree of drug encapsulation is particularly noteworthy. It has been found with the present invention that manufacture using the cosolvent system processing technique previously described is conducive to manufacture of the multi-component particles with a high degree of drug encapsulation. Furthermore, even when using the cosolvent system, the degree of encapsulation is often enhanced by operation of the manufacture process under controlled conditions, such as by acidification of the co-solvent system and/or preferred orientation of the flow of the feed solution to the flow of the anti-solvent, as previously discussed. Furthermore, by varying manufacture conditions, it is possible to vary the degree of encapsulation. For example, The degree of drug encapsulation desired in the multi-component powder will depend upon the drug release characteristics desired for the particular application of interest. For some applications it may be desirable that at least some of the drug immediately release for immediate therapeutic effect, and that the remaining drug be released over a longer period to prolong the therapeutic effect. In most instances, however, the multi-component powder will typically have a degree of drug encapsulation of larger than about 30%, preferably larger than about 50%, more preferably larger than about 60%, still more preferably larger than about 70%, and most preferably larger than about 80%. In some instances, the degree of drug encapsulation may be larger than about 90%.

The biocompatible polymer may be any suitable biocompatible polymer. Exemplary biocompatible polymers are as previously described in the discussion concerning the manufacture method. Furthermore, the multi-component particles may include the biocompatible polymer and the drug in any desired proportions, such as those previously described in the discussion concerning the manufacture method.

In another aspect, the present invention provides a packaged drug-containing powder product, with at least one powder batch contained within a receptacle, that is either a part of or adapted to be operable with an inhaler, most typically a dry powder inhaler capable of generating a drug-containing aerosol for pulmonary delivery of the drug to a subject when inhaled by the subject. The product includes a drug-containing powder of the present invention, as described previously, contained within the receptacle in a manner so that at least a portion of the drug-containing powder is removed from the receptacle and aerosolized by the inhaler when the inhaler is actuated. The drug-containing powder contained in the receptacle may be any drug-containing powder of the present invention, such as, for example, substantially pure drug powder or multi-component powder including drug and a biocompatible polymer. In a preferred embodiment, however, the drug-containing powder is a multi-component powder including a degree of drug encapsulation of at least about 50%.

The receptacle may be any suitable receptacle that is adapted to be received by and to operatively cooperate with an inhaler, so that the inhaler is capable of being actuated to remove at least a portion of the drug-containing powder from the receptacle to generate an aerosol including drug-containing particles dispersed in a carrier gas, for inhalation by a subject for pulmonary delivery of drug. Therefore, the receptacle for any particular embodiment will typically be designed for use with a particular dry powder inhaler. Several different inhaler/receptacle designs are known in the art, and any such receptacle may be used with this aspect of the present invention. Furthermore, the present invention includes receptacle designs that will inevitably be designed in the future to cooperate with new inhaler designs.

In one embodiment, the receptacle contains at least one compartment including a unit dose of drug, meaning that actuation of the inhaler to produce an aerosol from the drug-containing powder contained in the compartment will result in production of an aerosol containing a quantity of drug sufficient to provide substantially only a single therapeutically effective dose of drug to a subject when the aerosol is inhaled by the subject. In a preferred embodiment, the receptacle is a multi-compartment receptacle and includes a plurality of such compartments, with each compartment including a unit dose of drug, so that when the receptacle is operably received by an inhaler, the inhaler is capable of being sequentially actuated, with each actuation aerosolizing drug-containing powder from a different one of the compartments to provide an aerosol with a single dose of drug for inhalation by a subject. For example, one type of multi-component receptacle is a multi-compartment blister pack adapted to be received by and to operably cooperate with a dry powder inhaler. Such a multi-component blister pack could be made in any convenient geometric form as dictated for use with any particular inhaler design, such as, for example, in the form of a blister ring, a blister disk, or a blister strip. Another type of multi-component receptacle is a multi-compartment cartridge. Such cartridges may be made in any convenient geometric form as dictated for use with any particular inhaler design, such as, for example, in the form of a cartridge ring, cartridge disk or cartridge strip. As will be appreciated, the compartment(s) of the receptacle may be sealed to protect the drug prior to use, or may be unsealed, but enclosed within the inhaler in a manner to adequately protect the drug. In one embodiment, the receptacle acts to transfer measured quantities of drug-containing powder from a bulk reservoir of powder contained within the inhaler for use to produce unit dose aerosols when the inhaler is actuated. In a preferred embodiment, however, the compartment(s) of the receptacle will each initially be filled with a unit dose of drug and will each be sealed substantially until aerosolization of the unit dose when the inhaler is actuated.

As will be appreciated, any number of designs and particular structures are possible for such a multi-compartment receptacle. Nonlimiting examples of suitable multi-component receptacles, and corresponding dry powder inhalers, useful with the present invention are disclosed in U.S. Pat. No. 5,503,869 (various medicament carrier cassette designs); International Patent Publication No. WO 98/04308 (various medicament carrier cassette designs); European Patent Publication EP 0 069 715 (perforated membrane); U.S. Pat. No. 5,460,173 (screened disc structure), U.S. Pat. No. 5,619,984 (flexible carriers), U.S. Pat. No. 5,794,613 (disc-shaped disperser with multiple cavities); and U.S. Pat. No. 5,875,776 (dosing carousel).

In one particularly preferred embodiment, the receptacle is a capsule containing a unit dose of the drug, with the capsule designed for use with a dry powder inhaler that aerosolizes the powder from the capsule by making air entry and exit holes in the capsule and moving air through the capsule during operation that causes the powder to be transported to the capsule extremity. Reference is made to U.S. Pat. Nos. 5,673,686 and 5,881,721, the contents of both of which are hereby incorporated herein in their entireties as if set forth herein in full at this location, for examples of the capsules and compatible inhalers useful with the present invention.

In another aspect, the present invention provides an apparatus for pulmonary delivery of drug. A drug-containing powder of the present invention, as described previously, is disposed within an inhaler that is actuatable to aerosolize at least a portion of the powder to produce an aerosol including substantially a single dose of a therapeutically effective amount of drug inhalable by a subject. The drug-containing powder is preferably contained within a receptacle, as previously described, operably engaged with or being an integral part of the inhaler. In a preferred embodiment, the receptacle is a multi-component receptacle, as previously described, with each component including a unit dose powder batch, and the inhaler is successively actuatable, so that each successive actuation aerosolized at least a portion of a powder batch in a different one of the compartments. In another embodiment, however, the inhaler may be a single dose inhaler, meaning that the receptacle is a single compartment receptacle including only a single unit dose of drug. This would be the case, for example, when the inhaler is a single use inhaler, which could be designed to be disposable or refillable after the single use. The inhaler may be any desired inhaler design. In a preferred embodiment, the inhaler will be a dry powder inhaler. In another embodiment, the inhaler will be a metered dose inhaler, in which the drug-containing powder is suspended in a propellant fluid that is in a liquid state prior to actuation and which expands and substantially vaporizes when the inhaler is actuated to produce an aerosol. The propellant fluid may be a halocarbon, such as fluorochlorocarbons currently being phased out, or new classes of propellant fluids being identified to replace fluorochlorocarbons.

A preferred inhaler for use with the present invention is one capable of aerosolizing the powder from a chamber, preferably a capsule, in a manner to move the powder to the extremity of the chamber to break up the powder to appropriate size for aerosolization. This is particulary the case with the particles of the present invention that are formed as large particle units that break apart during the aerosolization. Exemplary preferred inhalers, which have been found to work particularly well with the present invention are as described in U.S. Pat. Nos. 5,673,686 and 5,881,721, the entire contents of both of which are incorporated herein as if set forth in full at this location.

Figure 4:
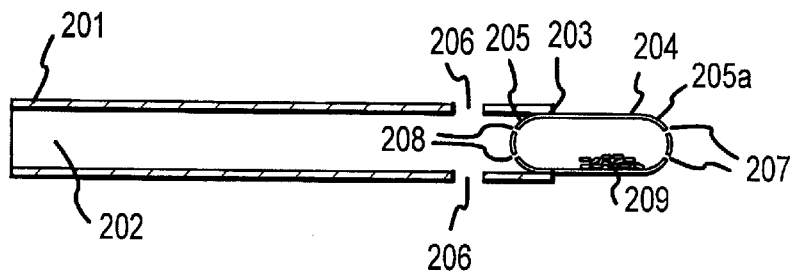

Referring now to FIGS. 4–11, an inhaler and related components, preferred for use with the present invention, as set forth in U.S Pat. No. 5,673,686 is partially described. As shown in FIG. 4, a gelatin capsule 204 is snugly fitting and held in remote end 203 of the tube 202. Near the inner end 205 of capsule 204 are two air-inlet orifices 206 in the tube 201.

Capsule 204 is a conventional capsule of two parts with rounded ends 205. Outer end 205a has two holes 207 therein and inner end 205 has four holes 208 therein. (See also FIGS. 7 and 8). The holes are the same size (although they need not be). For a standard no. 4 capsule (14 mm×5 mm), the hole size can be 0.65 mm diameter for example. The capsule 204 contains a dose 209 of medicament, either pure or mixed in a carrier powder. The powder should preferably not fill more than about 10% of the volume of the capsule, to provide adequate space for aerosolization of the powder during use.

Figure 5:
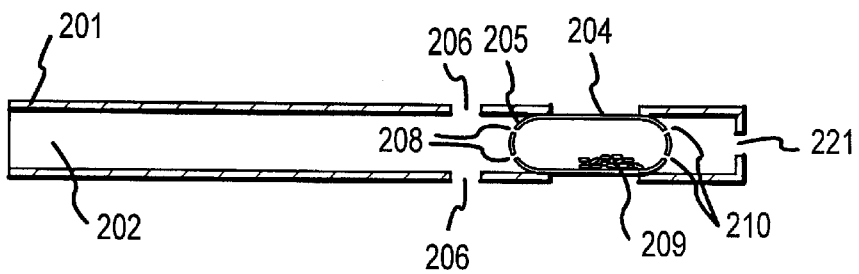

FIG. 5 differs from FIG. 4 in that a cover 220 is provided over the outer end 205a of capsule 204, which end may have the same number of holes 210 therein as inner end 205. Cover 220 has a restricted air orifice 221.

Figure 6:
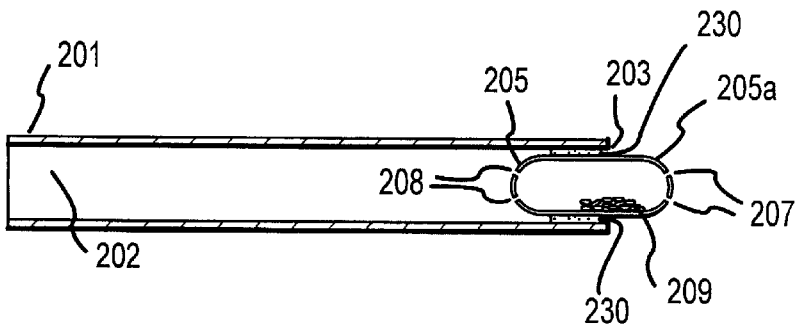
Figure 7:
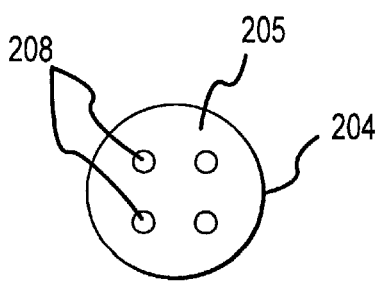
Figure 8:
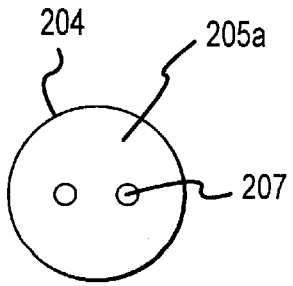

FIG. 6 differs from FIG. 4 in that air inlets 206 have been omitted and, instead, inner radial fins 230 are provided at end 203 of tube 201 to hold the capsule 204 spaced from the inner wall of the tube and so provide an air inlet passages between the periphery of the capsule 204 and the tube 201.

FIGS. 9–11 illustrate another embodiment of an inhaler useful with the invention. In these Figures, like numerals indicate like parts.

FIG. 9 shows the inhaler 270 comprising a capsule reservoir cap 271, a rotatable barrel member 272 and mouthpiece member 273. Mouthpiece member 273 includes a capsule ejection orifice 274 and an inhalation orifice 275. Barrel member 272 includes a series of external ribs 276 for improved manual grip.

FIG. 10 is an exploded perspective view of the inhaler of FIG. 9 showing its components. Capsule reservoir cap 271 comprises a cylindrical cap member closed at one end 280, the other end 281 being open and containing internally thereof short screw-threads 282. Reservoir support body 283 is of circular cross-section and includes a series of short screw-threads 284 on the periphery thereof for mating engagement with threads 282 on reservoir cap 271. Support body 283 is formed on its forward face 289 with an axial hole 285 keyed to receive one end of axle 286. Offset from axial hole 285 is a through-bore 287 opening in an upstanding cylindrical sleeve on rear face 290. Receivable in sleeve 288 is a cylinder 291 having a supply of capsules 292, stacked endwise.

Support member 283 also has two other upstanding cylindrical sleeves 293, 294 on its rear face 290, which receive and close the ends of spare capsule supply cylinders 295, 296. Mounted on front face 289 of support 283 is a cutting blade 297 projecting perpendicular to the face 289. Also on face 289 is an ejector ramp projection 350.

Barrel member 272 has an axial bore 300 in which is received axle 286 about which barrel member 272 is rotatable. Barrel 272 has an offset through-bore 301 which constitutes a container for receiving a capsule in use of the device. Around the periphery of cylindrical barrel 272 are external ribs 276. Each end face 302, 303 of the barrel has a peripheral upstanding wall 304, 305 of a height slightly greater than the projecting length of blades 297, 310 so that the blades do not engage the respective ends faces 302, 303 of the barrel member.

Blade support member 311 is of a circular shape and has an axial bore keyed to one end of the axle 286. The member 311 has a first through bore 312 and a second through bore 313. Projecting from member 311 has two air inlets (not shown in FIG. 10; see FIG. 11), which are straight bores perpendicular to the axis of first through bore 312.

Mouthpiece 273 is joined face to fact to support member 311. Mouthpiece 273 has a first through bore 320 which constitutes an inhalation tube terminating at inhalation orifice 275 and a second through bore 321 which is a used capsule ejection bore, and terminates at capsule ejection orifice 274. A cap 330 can be provided to cover the mouthpiece 273 when the device is not in use, the cap including a pocket clip 331.

The assembly and operation of the device are as follows: Cylinder 291 containing a supply of powder containing capsules 292 is located in sleeve 288 and a capsule moves under gravity into bore 287 of body 283. Barrel 272 is rotated with respect to supports 283 and 311, about axle 286, to bring bore 301 into line with bore 287. The capsule enters and is fully received into the barrel member. The capsule is slightly longer than the distance between the end faces 302, 303.

The barrel has a ratchet (or other device) associated therewith whereby it can be rotated about axle 286 in one direction only and in stepwise motion. The ratchet is not shown. The barrel is now rotated and this brings each projecting end of the capsule, in turn, into engagement with a respective knife member 297, 310. The ends of the capsule are thus slit (see slits 340, 341 in FIG. 11).

The barrel is now advanced further, to bring the capsule into alignment with bore 312 of support 311. The unit is now ready for inhalation. The user inserts the end of the mouthpiece 373 into his/her mouth and inhales. Air is drawn through inhalation tube 320 and bore 312 and thus through bore 301 in barrel 272. The suction draws the capsule forward to enter bore 312 and engage closely the end of bore 320 (see FIG. 11). To facilitate seating of the end of the capsule in bore 320, the end of the bore can be flared at 342 (FIG. 11).

The air flowing through the mouthpiece enters the device primarily through the path of least resistance, which is through air inlets 343 but also, in a smaller amount, through the slits in the capsule. Thus air is drawn through the capsule entering at slit 340 and exiting with the entrained powder at slit 341, for passage via bore 312, where a considerable amount of air is admitted through inlets 343. The air flow entraining the powder now enters bore 320 of the mouthpiece for passage into the user's mouth. As barrel 372 is transparent, the user can repeat the inhalation operation for as long as powder remains visible inside the capsule.

Finally, after the contents of the capsule have been inhaled and the suction has stopped, the empty capsule falls away from the flared end of bore 320 into the barrel bore 301. The barrel then continues to be rotated in the same direction as before to bring the capsule, still in bore 301 into line with the ejection bore 313. Simultaneously, the rearward end of the capsule is engaged by ejector ramp projection 350 which pushes the spent capsule out of ejection orifice 274. Barrel 272 is now rotated to bring the empty bore 301 into registry with bore 287 to receive another capsule from reservoir cylinder 291. When the cylinder is empty, cap 271 is removed and tube 291 is replaced by one of cylinders 295, 296.

The device of FIG. 10 relies on gravity for loading and ejecting capsules; therefore these operations have to be conducted with the device held close to the vertical. The operations of cutting the capsule and inhaling it can be done with the device held in any position.

Referring now to FIGS. 12–16, an inhaler and related components, particularly preferred for use with the present invention, as set forth in U.S Pat. No. 5,881,721 is partially described.

FIGS. 12, 13 and 14 illustrate different perspectives of the ramp, having a straight and flat face 401 and a capsule passage 402. The dimensions of one embodiment of the present invention have been measured and correspond to the letter references inscribed in FIGS. 12, 13 and 14 and disclosed in Table 1:

TABLE 1

| Diameter of the cylindrical tube | cy | 16 mm |
| --- | --- | --- |
| Capsule hole diameter | hw | 7 mm |
| Ramp height | rh | 26 mm |
| Ramp angle | N | 30° |
| Distance from the beginning of the ramp to the beginning of the hole | rb | 16 mm |
| Distance from the beginning of the hole to the lower edge of the hole | bl | 11 mm |

These dimensions are adequate for the correct movement of a pharmaceutical capsule measuring 14.2 mm in length and 5.3 mm in width. However, it should be stressed that proper adaptation of these dimensions to objects with different sizes is readily possible without undue experimentation. Therefore, this invention is not restricted to one capsule size only and not even to capsules: pharmaceutical unit doses or sweets having the general shape of a capsule will equally be usable in the present invention and benefit from it.

FIG. 15 shows the inhaler comprised of a mouthpiece M, a barrel area B, a ramp area R, free headspace H and a capsule container C. The capsule container 404 is filled to the brim with capsules 405.

FIG. 16 shows the same inhaler which has been turned upside down. The capsules now fill the free headspace and the ramp area and become vertically oriented as they near the passage 409. One capsule 408 is already inserted into the passage 409 and its movement is blocked by the capsule 406 which has preceded it and been dispensed into the capsule chamber 407. The capsule chamber 407 is contained inside a rotating barrel 410.

The operation of the inhaler requires that once a capsule has been loaded into the capsule chamber 407, the rotating barrel 410 is turned. This movement transports the capsule 406 past two small blades (not shown) which will slit both ends, will then take it to the inhalation position, and finally, after inhalation has taken place, to the ejection position 411. Continuing to turn the rotating barrel 410 will bring the capsule chamber 407 in alignment again with the passage 409 where the next capsule 408 is in place for dispensing.

The rotating barrel 410 is connected to the cylindrical tube 412 and is unconnected to the ramp 413. In operation, the turning motion of the rotating barrel 410 and cylindrical tube 412 is in opposite direction to that of the ramp 413. These opposite turning motions will further assist the righting of the capsules between the ramp 413 and the cylindrical tube 412 and dispensing of the capsule into the passage 409.

The inhaler, as just described, and especially including the embodiments as described further in U.S. Pat. Nos. 5,673, 686 and 5,881,721, including capsules having disposed therein the particulate product described herein is a particularly important aspect of the present invention. In particular, the particulate product of the present invention as loaded in the capsules and the inhaler includes the aggregate units described herein, which break down to smaller particles during aerosolization.

EXAMPLES

The examples presented below are representative of certain aspects of the present invention and are not intended to demonstrate every aspect of the present invention. These examples are provided to further aid understanding of the present invention, and are not limiting of the scope of the present invention.

The materials used in the examples are as follows:

| | |
|---|---|
| DMSO: | Reagent grade from Sigma-Aldrich Corp. (Aldrich) |
| HCl: | Reagent grade from Fisher Scientific International Inc. (Fisher) |
| Chloroform | HPLC grade from Fisher |
| Methanol (MeOH): | HPLC grade from Fisher |
| Isopropyl alcohol (i-PrOH): | HPLC grade from Fisher |
| Methylene chloride (MeCl$_2$): | HPLC grade from Fisher |
| Acetonitrile: | HPLC grade from Fisher |
| Carbon dioxide: | USP grade from General Air, Inc. |
| Bovine insulin: | Pancreas derived bovine insulin (zinc salt form) from Sigma |
| Human insulin: | Recombinant human insulin (zinc salt form) from Sigma |
| Poly(l-lactic acid) (L-PLA): | Medical grade from Boehringer Ingelheim |
| Dibasic sodium phosphate septahydrate: | Reagent grade from Fisher |
| Sodium chloride: | Reagent grade from Fisher |
| Potassium chloride: | Reagent grade from Fisher |
| Tween 20 ™: | Enzyme grade from Fisher |
| Monobasic potassium phosphate: | Reagent grade from Fisher |
| Sodium azide: | Reagent grade from Aldrich |

Example 1

This example demonstrates manufacture of single-component powders including substantially only insulin according to the manufacture method of the present invention using a feed solution including a cosolvent system.

Feed solutions are prepared including insulin dissolved in a variety of cosolvent systems at a concentration of about 1–2 mg/mL. The feed solution is contacted in countercurrent flow with supercritical compressed carbon dioxide as an anti-solvent flowing through a precipitation chamber at a temperature of about 37±2° C. and a pressure of about 83.6±1.4 atm to precipitate insulin from the feed solution. The precipitation chamber is a stainless steel chamber about 20 cm long and having a square cross-section of about 2 cm by 2 cm. The compressed carbon dioxide is delivered to the chamber via a pressure regulator and is introduced into the top of the chamber. The feed solution is delivered to the chamber via a syringe pump and is introduced into the flowing carbon dioxide anti-solvent in countercurrent flow though a 160 micron diameter stainless steel capillary tube located in the upper part of the chamber approximately in the middle of the stream of flowing carbon dioxide anti-solvent. The flow rate of the carbon dioxide is maintained at about 50±1 mL/min and the flow rate of the feed solution is maintained at about 1±0.1 mL/min. The precipitated particles are collected on either a polyvinylidene fluoride (PVDF) filter or a polytetrafluoroethelyne (PGLP) filter (0.2micron) located outside of the chamber.

As shown in Table 1, tests 1–4 are comparative tests using DMSO, DMFA or methanol as the only solvent in the feed solution, with tests 2–4 including addition of a small quantity of HCl (2.4 mM in feed solution). Tests 5–11 demonstrate processing using a cosolvent system with DMSO as the first organic solvent and methanol, isopropyl alcohol, methylene chloride, (iPrOH), methylene chloride (CH$_2$Cl$_2$) or acetonitrile—as the second organic solvent.

For the comparative tests (Tests 1–4), the feed solutions are each prepared by dissolving the insulin in the organic solvent at room temperature with stirring, with the first organic solvent being preacidified with the HCl when used. For the tests involving use of a cosolvent system, the feed solutions are each prepared by first dissolving the insulin in the first organic solvent (DMSO) at room temperature with stirring. To this solution is then slowly added the second organic solvent with stirring and the resulting mixture is stirred for an additional 10 minutes prior to loading into the syringe pump.

Results of the tests are shown in Table 2. As seen in Table 2, the powders prepared in the comparative tests are non-free flowing and are not desirable for use in pulmonary delivery applications. The powders prepared using the cosolvent system (tests 5–12) are free-flowing powders and more desirable for use in pulmonary delivery applications. Test 13 shows the detrimental impact on powder quality of including 5% water in a cosolvent system including DMSO and methanol.

Moreover, it is noted that during the preparation of the feed solutions for tests 6 through 12, insulin precipitated to form a colloidal suspension in the feed solution when the isopropyl alcohol was added to the DMSO/insulin solution. These tests also result in preparation of free flowing powders.

TABLE 2

| Test | Solvent System | Insulin Source | Powder Characteristics |
|---|---|---|---|
| 1 | DMSO | Bovine | Granular non-free flowing powder |
| 2 | DMSO, HCl (2.4 mM) | Bovine/Human | Granular non-free flowing powder |
| 3 | DMF, HCl (2.4 mM) | Bovine | Granular non-free flowing powder |
| 4 | MeOH, HCl (2.4 mM) | Bovine | Fluffy non-free flowing powder |
| 5 | DMSO, MeOH (50:50) | Human | Fluffy free flowing powder |
| 6 | DMSO, iPrOH (50:50) | Human | Fine free flowing powder |
| 7 | DMSO, iPrOH (40:60) | Human | Fine free flowing powder |
| 8 | DMSO, iPrOH (20:80) | Human | Fine free flowing powder |
| 9 | DMSO, iPrOH (10:90) | Human | Fine free flowing powder |
| 10 | DMSO, CH$_2$Cl$_2$ (50:50) | Human | Fluffy free flowing powder |
| 11 | DMSO, Acetonitrile (50:50) | Human | Fluffy free flowing powder |
| 12 | DMSO, McOH (20:80) | Human | Fluffy free flowing powder |
| 13 | DMSO, MeOH, H$_2$O (20:75:5) | Human | Gummy material |

Example 2

This example demonstrates the manufacture of multi-component particles including insulin and a biocompatible polymer according to the manufacture method of the present invention using a feed solution including a cosolvent system.

Feed solutions are prepared including various molecular weight poly(L-lactic acid) and human insulin in different solvent systems. Tests 14 and 15 are comparative tests using a single solvent (DMSO), while tests 16–37 use various cosolvent systems with either DMSO or methanol as the first organic solvent and methylene chloride as the second organic solvent. Insulin loading is varied from 7% to 50% by weight (based on weight of insulin relative to total weight of insulin medium plus polymer). Each feed solution is prepared in 50 mL batches generally by the following procedure: DMSO or methanol is acidified with concentrated HCl to provide the desired level of acidification and the insulin is then dissolved into the resulting acidified solvent with stirring at room temperature. For comparative tests 14 and 15, the desired amount of the polymer is then dissolved in the insulin/DMSO solution with stirring at room temperature. For the other tests, the polymer is instead dissolved in methylene chloride in a separate container to form a second solution with stirring at room temperature. The polymer/methylene chloride solution is then slowly added to the insulin/DMSO or the insulin/methanol solution, as the case may be, with stirring at room temperature, with the resulting mixture being stirred an additional 2–5 minutes prior to being loaded into the syringe pump. The quantities of ingredients per 50 mL batch for each test is shown in Table 3.

The feed solutions are contacted with compressed carbon dioxide anti-solvent under conditions similar to those described for Example 1. For each powder, the degree of insulin encapsulation is determined by in vitro testing involving immersing a 6 mg sample of the powder in 30 mL of PBS (prepared as previously described to include 137 mM NaCl, 10.2 mM $Na_2HPO_4 \cdot 7H_2O$, 1.8 mM $KH_2PO_4$, 2.7 mM KCl and 3.1 mM $NaN_3$) and determining the percentage of insulin dissolution into the PBS according to the procedure previously described by monitoring insulin concentration in the PBS by HPLC analysis. Tests 14 and 15 are comparative tests demonstrating use of a single-solvent system (DMSO).

Figure 3:
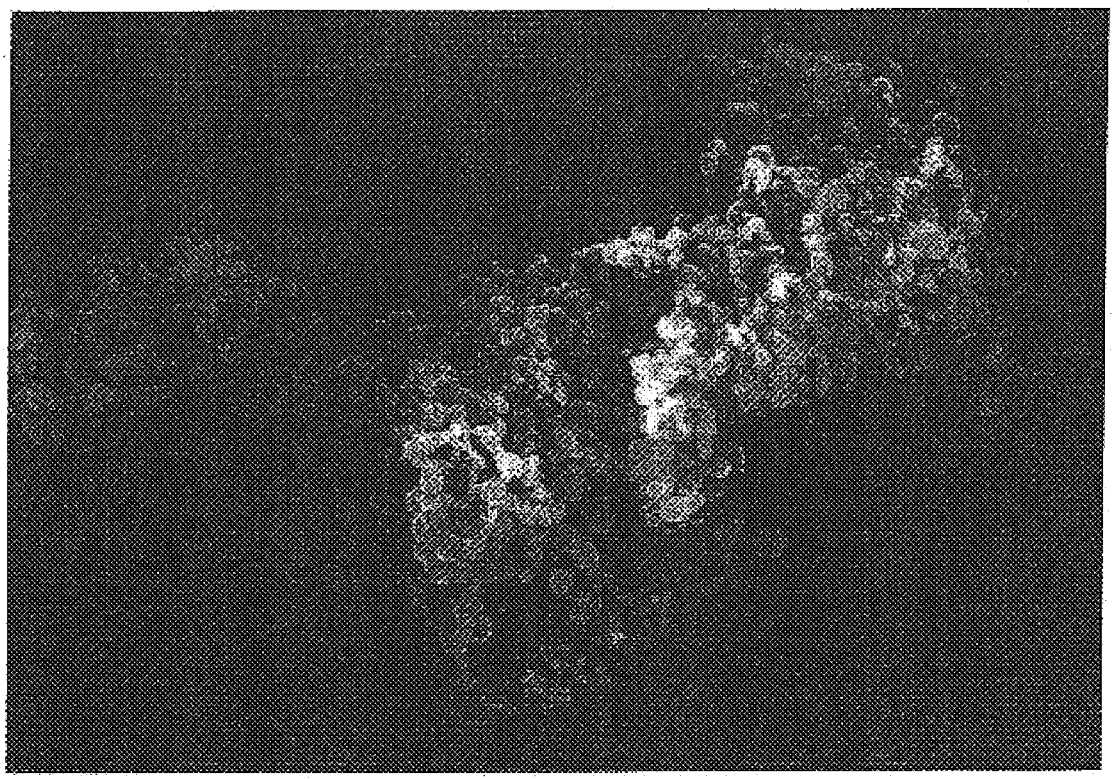

A summary of the solvent systems and results of the tests are shown in Table 4. As shown in Table 4, substantial encapsulation of the insulin is more difficult to obtain when using low molecular polymers. It is also seen, however, that the use of a cosolvent system generally results in significantly higher insulin encapsulation than the single solvent, especially for tests using higher molecular weight polymer. Also, the tests using methanol and methylene chloride in the cosolvent system generally show a higher degree of insulin encapsulation than the tests using DMSO and methylene chloride in the cosolvent system. Furthermore tests 21, 25, and 35–37 show preparation of powders having over 50% insulin encapsulation even when the powders include high levels of insulin loading. Table 4 also shows the level of burst demonstrated by each of the powders during the in vitro testing. The burst is the percentage of the insulin that is released during the first 15 minutes after immersion in of the sample the PBS. FIG. 3 shows a photomicrograph of a representative sample from test 33 showing an aggregate of the particulate product comprised of micron to submicron primary particles. The main body of the aggregate structure has a width of about 10 microns and a length of about 40 microns.

TABLE 3

| Test | DMSO (mL) | MeOH (mL) | Conc. HCl (uL) | $CH_2Cl_2$ (mL) | Insulin (mg) | Polymer (mg) | Polymer MW (kDa) |
|---|---|---|---|---|---|---|---|
| 14 | 250 | 0 | 25 | 0 | 504 | 500 | 2 |
| 15 | 116 | 0 | 30 | 0 | 405 | 408 | 26 |
| 16 | 98 | 0 | 10 | 2 | 201 | 201 | 26 |
| 17 | 98 | 0 | 10 | 6 | 201 | 611 | 100 |
| 18 | 90 | 0 | 10 | 10 | 200 | 201 | 26 |
| 19 | 50 | 0 | 10 | 50 | 203 | 207 | 2 |
| 20 | 50 | 0 | 10 | 50 | 208 | 203 | 26 |
| 21 | 50 | 0 | 10 | 50 | 202 | 201 | 100 |
| 22 | 25 | 0 | 10 | 75 | 201 | 203 | 2 |
| 23 | 25 | 0 | 10 | 75 | 101 | 1001 | 2 |
| 24 | 25 | 0 | 10 | 75 | 100 | 994 | 100 |
| 25 | 0 | 10 | 10 | 90 | 61 | 204 | 100 |
| 26 | 0 | 40 | 10 | 60 | 60 | 742 | 100 |
| 27 | 0 | 15 | 10 | 85 | 60 | 749 | 100 |
| 28 | 0 | 15 | 10 | 85 | 60 | 202 | 100 |
| 29 | 0 | 70 | 20 | 186 | 141 | 1878 | 100 |
| 30 | 0 | 27 | 10 | 73 | 56 | 728 | 100 |
| 31 | 0 | 14 | 10 | 37 | 27 | 365 | 100 |
| 32 | 0 | 28 | 10 | 74 | 62 | 446 | 100 |
| 33 | 0 | 28 | 20 | 74 | 61 | 459 | 100 |
| 34 | 0 | 14 | 20 | 37 | 51 | 354 | 100 |
| 35 | 0 | 56 | 40 | 148 | 126 | 376 | 100 |
| 36 | 0 | 40 | 20 | 60 | 201 | 203 | 100 |
| 37 | 0 | 14 | 20 | 37 | 195 | 191 | 100 |

TABLE 4

| Test | Solvent System | | | | Insulin Load (%) | Insulin Burst (%) | Insulin Encapsulation (%) |
| | DMSO (%) | MeOH (%) | $CH_2Cl_2$ (%) | HCl (mM) | | | |
|---|---|---|---|---|---|---|---|
| 14 | 100 | 0 | 0 | 1.2 | 50 | 100 | 0 |
| 15 | 100 | 0 | 0 | 1.8 | 50 | 72 | 28 |
| 16 | 98 | 0 | 2 | 1.2 | 50 | 73 | 27 |
| 17 | 94 | 0 | 6 | 1.2 | 25 | 85 | 15 |
| 18 | 90 | 0 | 10 | 1.2 | 50 | 86 | 14 |
| 19 | 50 | 0 | 50 | 1.2 | 50 | 100 | 0 |
| 20 | 50 | 0 | 50 | 1.2 | 51 | 76 | 24 |
| 21 | 50 | 0 | 50 | 1.2 | 50 | 49 | 51 |
| 22 | 25 | 0 | 75 | 1.2 | 50 | 100 | 0 |
| 23 | 25 | 0 | 75 | 1.2 | 9 | 66 | 34 |
| 24 | 25 | 0 | 75 | 1.2 | 9 | 51 | 49 |
| 25 | 0 | 10 | 90 | 1.2 | 23 | 11 | 89 |
| 26 | 0 | 40 | 60 | 1.2 | 8 | 43 | 57 |
| 27 | 0 | 15 | 85 | 1.2 | 7 | 20 | 80 |
| 28 | 0 | 15 | 85 | 1.2 | 23 | 56 | 44 |
| 29 | 0 | 27 | 73 | 0.9 | 7 | 50 | 50 |
| 30 | 0 | 27 | 73 | 1.2 | 7 | 37 | 63 |
| 31 | 0 | 27 | 73 | 2.4 | 7 | 15 | 85 |
| 32 | 0 | 27 | 73 | 1.2 | 12 | 24 | 76 |
| 33 | 0 | 27 | 73 | 2.4 | 12 | 1 | 99 |
| 34 | 0 | 27 | 73 | 4.8 | 13 | 26 | 74 |
| 35 | 0 | 27 | 73 | 2.4 | 25 | 7 | 93 |
| 36 | 0 | 40 | 60 | 2.4 | 50 | 40 | 60 |
| 37 | 0 | 27 | 73 | 4.8 | 50 | 34 | 66 |

Example 3

This example demonstrates sustained release of insulin in animal studies by pulmonary delivery using multi-component particles including insulin and a biocompatible polymer.

A powder of substantially pure insulin, of the type as prepared in Test 2 shown in Example 1, and a powder of multi-component particles, of the type as prepared in Test 33 of Example 2 (including 12% by weight insulin and 88% by weight of 100 k Da L-PLA), are administered intratracheally to male rabbits. Blood samples are taken prior to administration and periodically over a 24 hour period following administration and analyzed for insulin concentration.

Male rabbits weighing about 3 Kg are treated and/or anesthetized with atropine (subcutaneous), acepromazine (intramuscular) and halothane (inhalation). Intratracheal insulin placement is accomplished using a pediatric bronchoscope. An aqueous suspension of the powder (11.16 mg powder/mL of saline) is administered with a syringe and catheter placed inside an endotracheal tube. Each rabbit receives 12.5 units of insulin per Kg of animal weight. Periodically, 1.5 mL blood samples are collected from blood vessels in the ear and placed in EDTA tubes. Plasma is separated from each blood sample and tested for insulin concentration by radio immunoassay.

Figure 2:
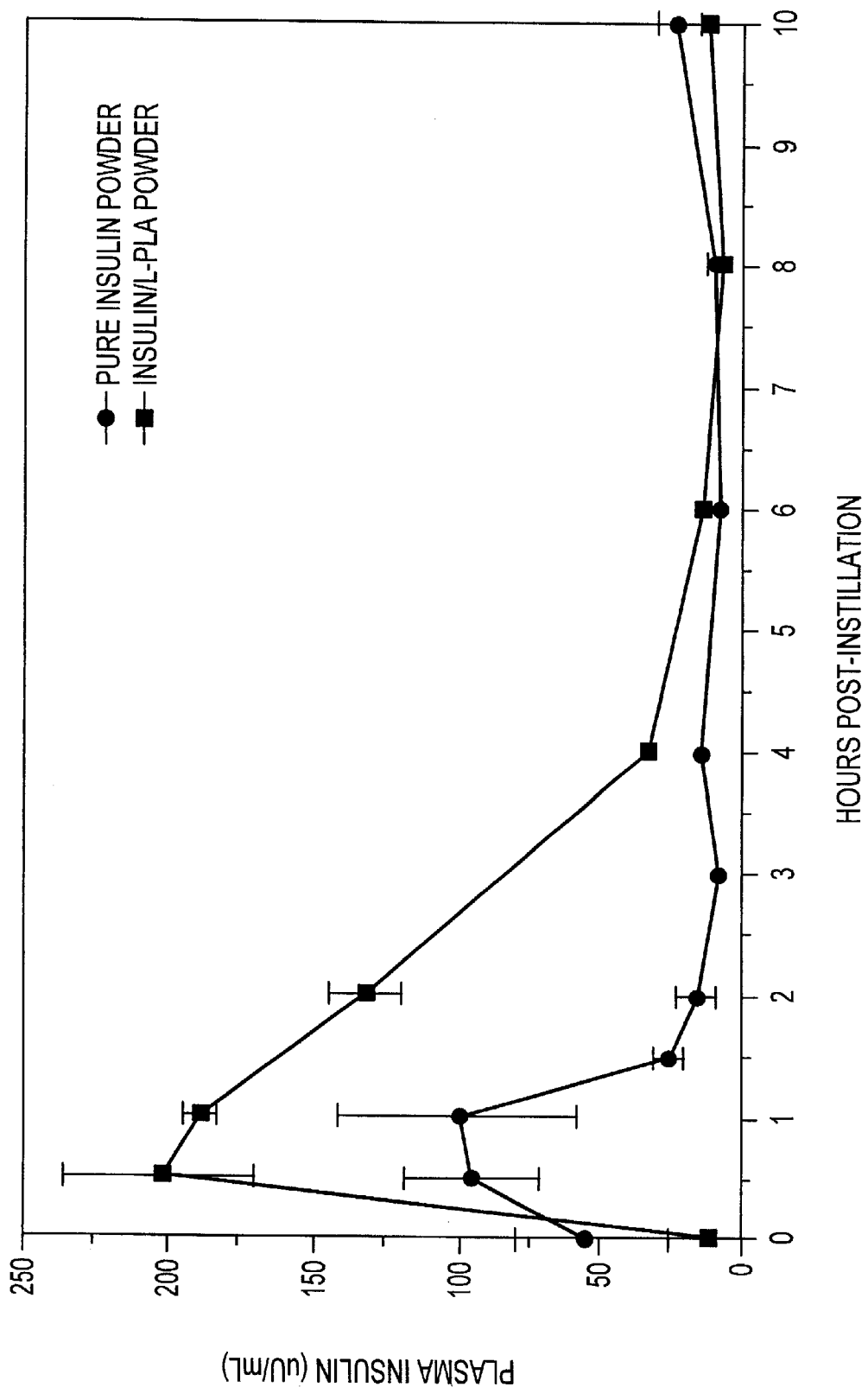

FIG. 2 shows a plot of measured insulin concentration in the plasma in microunits of insulin per mL of plasma for each of the pure insulin powder and the encapsulated insulin powder over a period of 8 hours following intratracheal placement. As seen in FIG. 2, use of the encapsulated insulin powder results in the presence of a significantly elevated insulin concentration in the plasma for an extended time relative to the pure insulin powder.

Example 4

Insulin and glucagon powders are prepared with compositions as shown in Table 5. The insulin (test 38) is processed in a cosolvent system of 20 wt. % DMSO and 80 wt. % isopropyl alcohol, with no acid addition, including 2.1 mg/mL dissolved insulin. In test 39, a cosolvent system of 80 wt. % chloroform and 20% DMSO is used, with 0.51 mg/mL dissolved glucagon and 0.52 mg/mL dissolved DPPC (dipalmitoylphosphatidylcholine). In test 40, a cosolvent system of 50 wt. % chloroform and 50 wt. % DMSO is used, with 0.5 mg/mL dissolved glucagon and 0.25 mg/mL dissolved DPPC.

TABLE 5

| Test | Drug | Wt. % Drug | Other Component | Wt. % Other |
|---|---|---|---|---|
| 38 | Insulin | 100 | | |
| 39 | Glucagon | 50 | DPPC | 50 |
| 40 | Glucagon | 67 | DPPC | 33 |

Figure 18:
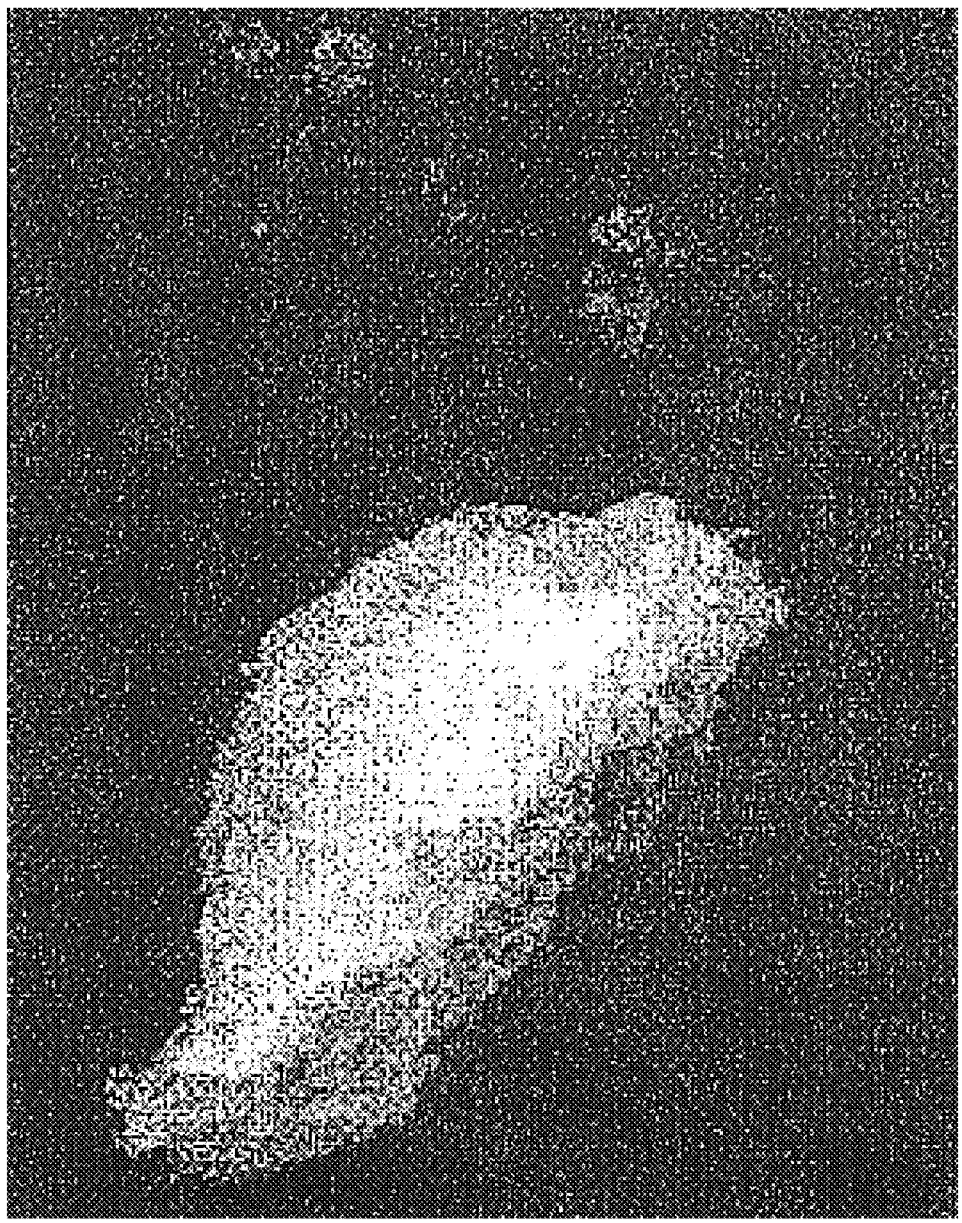
Figure 19:
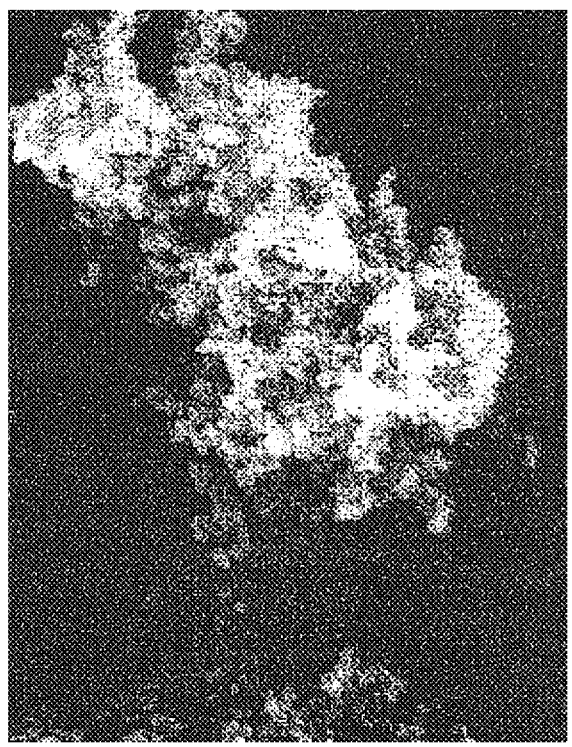
Figure 20:
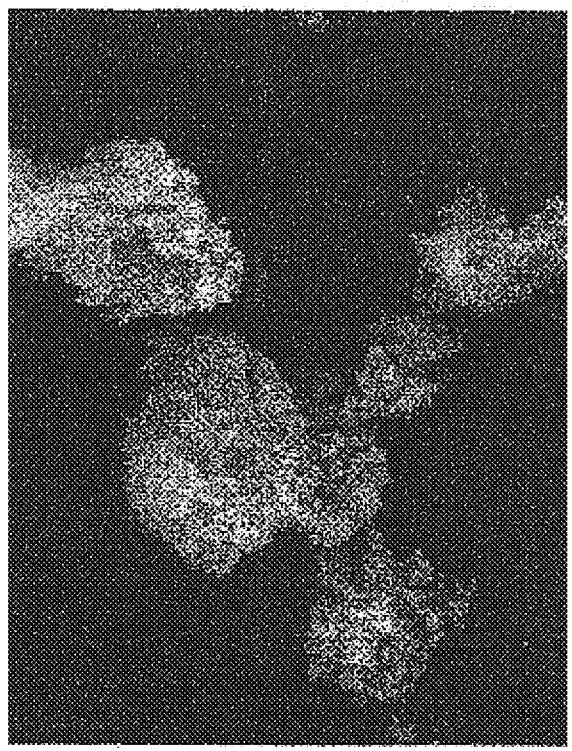

All of the powders include predominantly large particle units. FIG. 18 is a photomicrograph from the powder of Test 38, at 500×magnification, showing a large particle unit in the powder that is several hundred microns long. FIG. 19 is a photomicrograph from the powder of Test 39, at a magnification of 10,000×, showing a large particle unit in the powder that is approximately 15 microns long. FIG. 10 is a photomicrograph from the powder of Test 40, at a magnification of 1,000× showing large particle units on the order of about 40–80 microns in size. However when powders such as these are aerosolized, they demonstrate mass median aerodynamic diameters of less than about 6 microns, and typically much smaller, indicating the large particle units are broken apart during aerosolization.

Example 5

Powders generally produced using the 2 cm wide×20 cm long precipitation chamber of examples 1–4 typically exhibit tap densities significantly lower than 0.1 g/cm$^3$. Pure insulin and pure glucagon powders are prepared using instead a cylindrical precipitation chamber 5 cm in diameter and 1.5 cm long. Both the insulin and the glucagon are processed in a cosolvent system of 50 wt. % DMSO, 40 wt. % chloroform and 10 wt. % methanol. Both powders exhibit a tap density of about 0.2 g/cm$^3$.

While various embodiments of the present invention have been described in detail, it should be understood that any feature of any embodiment may be combined with any other feature of any other embodiment. For example, any compatible combination of cosolvent system, biocompatible polymer and drug loading may be processed according to the method of manufacture. Furthermore, any of the drug-containing particulate products may be incorporated into an inhaler or a receptacle adapted for use with an inhaler. Such compatible combinations are expressly included within the scope of the present invention. Moreover, while various embodiments of the present invention have been described in detail, it is apparent that modifications and adaptations of those embodiments will occur to those skilled in the art. It is to be expressly understood, however, that such modifications and adaptations are within the scope of the present invention, and it is intended that the appended claims be interpreted to the broadest coverage extent possible in light of applicable prior art.

What is claimed is:

1. A method for making a drug-containing particulate product, comprising:

contacting a drug-containing feed solution with a compressed anti-solvent fluid to precipitate drug-containing particles, the feed solution comprising the drug dissolved in mutually soluble solvents of a cosolvent system;

the mutually soluble solvents being mutually soluble when contacted with the compressed anti-solvent fluid during the contacting step and comprising at least a first organic solvent and a second organic solvent at a volume ratio of the second organic solvent to the first organic solvent in a range of from 10:90 to 99:1, the drug being at least an order of magnitude more soluble in the first organic solvent than the second organic solvent, and the second organic solvent being more readily extractable by the compressed anti-solvent fluid than the first organic solvent; and separating the drug-containing particles from the anti-solvent fluid.

2. The method of claim 1, wherein the volume ratio a the second organic solvent to the first organic solvent is larger than 30:70.

3. The method of claim 1, wherein the volume ratio of the second organic solvent to the first organic solvent is from 50:50 to 90:10.

4. The method of claim 1, wherein the first organic solvent is selected from the group consisting of DMSO and DMFA.

5. The method of claim 4, wherein the second organic solvent is an alcohol.

6. The method of claim 4, wherein the second organic solvent is a C1–C5 alkanol.

7. The method of claim 1, wherein the compressed anti-solvent, during the contacting, is at a reduced pressure of larger than 0.8 and a reduced temperature of larger than 0.95 the reduced pressure being a ratio of pressure expressed in atmospheres of the compressed anti-solvent during the contacting to the critical pressure expressed in atmospheres of the compressed anti-solvent, and the reduced temperature being a ratio of temperature expressed in K of the compressed anti-solvent during the contacting to the critical temperature expressed in K of the compressed anti-solvent.

8. The method of claim 7, wherein the reduced pressure of the compressed anti-solvent, during the contacting, is larger than 0.9.

9. The method of claim 7, wherein the compressed anti-solvent, during the contacting, is in a supercritical state.

10. The method of claim 7, wherein the compressed anti-solvent comprises compressed carbon dioxide.

11. The method of claim 1, wherein the compressed anti-solvent fluid consists essentially of only compressed carbon dioxide.

12. The method of claim 1, wherein the feed solution is substantially free of amphiphillic materials that improve solubility of the drug in the feed solution through hydrophobic ion pairing with the drug.

13. The method of claim 1, wherein, during the contacting step, the solution is introduced into a flow of the compressed anti-solvent fluid with a direction of flow of the solution being at an angle of from 45° to 180° relative to the direction of flow of the compressed anti-solvent fluid.

14. The method of claim 1, wherein the cosolvent system includes water, if at all, in an amount of smaller than 5 weight percent.

15. The method of claim 1, wherein the cosolvent system is substantially free of water.

16. The method of claim 1, wherein the drug is selected from the group consisting of a protein, a peptide and a genetic material.

17. The method of claim 1, wherein the drug is a protein.

18. The method of claim 1, wherein the drug is insulin.

19. The method of claim 1, wherein the concentration of the drug in the feed solution system is smaller than 0.3 mg of the drug per milliliter of the feed solution.

20. The method of claim 1, wherein, during the contacting step, the solution is introduced into the compressed anti-solvent fluid through an opening having a cross-sectional area available for flow of larger than 1 square millimeter.

21. The method of claim 1, wherein the contacting step is conducted under conditions so that the particles have a tap density of larger than 0.1 gram per cubic centimeter.

22. The method of claim 1, wherein the first organic solvent comprises DMSO and the second organic solvent comprises at least one of chloroform, methanol, ethanol and isopropanol.

23. The method of claim 1, wherein the feed solution comprises dipalmitoylphosphatidylcholine and the particles comprise at least a portion of the dipalmitoylphosphatidylcholine.

24. A particulate product comprising the particles made according to the method of claim 1.

25. The method of claim 1, wherein the drug is dissolved in the cosolvent system at a concentration in a range of from 0.1 mg to 5 mg of the drug per milliliter of the cosolvent system.

26. The method of claim 1, wherein the drug is dissolved in the cosolvent system at a concentration in a range of from 0.1 mg to 3 mg of the drug per milliliter of the cosolvent system.

27. The method of claim 1, wherein the second organic solvent is more volatile than the first organic solvent.

28. The method of claim 4, wherein the second organic solvent comprises at least one of chloroform, methanol, ethanol and isopropanol.

29. The method of claim 1, wherein the first organic solvent is DMSO.

30. A particulate product comprising the particles made according to the method of claim 2.

31. A particulate product comprising the particles made according to the method of claim 3.

32. A particulate product comprising the particles made according to the method of claim 4.

33. A particulate product comprising the particles made according to the method of claim 5.

34. A particulate product comprising the particles made according to the method of claim 6.

35. A particulate product comprising the particles made according to the method of claim 7.

36. A particulate product comprising the particles made according to the method of claim 8.

37. A particulate product comprising the particles made according to the method of claim 9.

38. A particulate product comprising the particles made according to the method of claim 10.

39. A particulate product comprising the particles made according to the method of claim 11.

40. A particulate product comprising the particles made according to the method of claim 12.

41. A particulate product comprising the particles made according to the method of claim 13.

42. A particulate product comprising the particles made according to the method of claim 14.

43. A particulate product comprising the particles made according to the method of claim 15.

44. A particulate product comprising the particles made according to the method of claim 16.

45. A particulate product comprising the particles made according to the method of claim 17.

46. A particulate product comprising the particles made according to the method of claim 18.

47. A particulate product comprising the particles made according to the method of claim 19.

48. A particulate product comprising the particles made according to the method of claim 20.

49. A particulate product comprising the particles made according to the method of claim 21.

50. A particulate product comprising the particles made according to the method of claim 22.

51. A particulate product comprising the particles made according to the method of claim 23.

52. A particulate product comprising the particles made according to the method of claim 25.

53. A particulate product comprising the particles made according to the method of claim 26.

54. A particulate product comprising the particles made according to the method of claim 27.

55. A particulate product comprising the particles made according to the method of claim 28.

56. A particulate product comprising the particles made according to the method of claim 29.

* * * * *

UNITED STATES PATENT AND TRADEMARK OFFICE
CERTIFICATE OF CORRECTION

PATENT NO. : 6,669,960 B2
DATED : December 30, 2003
INVENTOR(S) : Etter

It is certified that error appears in the above-identified patent and that said Letters Patent is hereby corrected as shown below:

<u>Column 28,</u>
Line 43, delete the word "a", and insert therefor -- of --.
Line 58, after the numbers "0.95", insert -- , --.

Signed and Sealed this

Thirteenth Day of April, 2004

JON W. DUDAS
*Acting Director of the United States Patent and Trademark Office*